(12) United States Patent
Kim et al.

(10) Patent No.: US 8,895,500 B2
(45) Date of Patent: *Nov. 25, 2014

(54) MODIFIED HUMAN TUMOR NECROSIS FACTOR RECEPTOR-I POLYPEPTIDE OR FRAGMENT THEREOF, AND METHOD FOR PREPARING SAME

(75) Inventors: Sung Wuk Kim, Gyeonggi-do (KR); Sung Soo Jun, Gyeonggi-do (KR); Seung Kook Park, Seoul (KR); Song Young Kim, Gyeonggi-do (KR); Eun Sun Kim, Gyeonggi-do (KR); Jae Kap Jeong, Gyeonggi-do (KR); Ha Na Kim, Gyeonggi-do (KR); Yeon Jung Song, Gyeonggi-do (KR)

(73) Assignee: Hanall Biopharma Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/822,775

(22) PCT Filed: Sep. 7, 2011

(86) PCT No.: PCT/KR2011/006621
§ 371 (c)(1),
(2), (4) Date: May 30, 2013

(87) PCT Pub. No.: WO2012/036410
PCT Pub. Date: Mar. 22, 2012

(65) Prior Publication Data
US 2013/0237472 A1    Sep. 12, 2013

(30) Foreign Application Priority Data

Sep. 13, 2010  (KR) .................. 10-2010-0089395

(51) Int. Cl.
| | | |
|---|---|---|
| *C07K 14/705* | (2006.01) | |
| *C07K 14/525* | (2006.01) | |
| *C12N 15/63* | (2006.01) | |
| *A61K 38/19* | (2006.01) | |
| *C07K 14/715* | (2006.01) | |
| *A61K 38/00* | (2006.01) | |

(52) U.S. Cl.
CPC ............. *C07K 14/7151* (2013.01); *A61K 38/19* (2013.01); *A61K 38/00* (2013.01); *C07K 14/705* (2013.01); *C07K 14/525* (2013.01); *C12N 15/63* (2013.01)
USPC ......... 514/1.5; 514/18.7; 514/19.2; 514/19.3; 514/19.4; 514/19.5

(58) Field of Classification Search
None
See application file for complete search history.

(56) References Cited

U.S. PATENT DOCUMENTS 6,989,147 B2   1/2006  Fisher et al.
7,144,987 B1 * 12/2006  Chirino et al. ................ 530/351
2004/0170975 A1  9/2004  Savitzky et al.

FOREIGN PATENT DOCUMENTS

EP    2221314 A1    8/2010

OTHER PUBLICATIONS

Wong et al., TNFalph blockade in human diseases: mechanism and future directions, Clin. Immunol. 126:121-136 (2008).*
Guicciardi et al., "Life and death by death receptors," FASEB J. 23:1625-1637 (2009).*
Gomez-Gallego et al., "Multiple Sclerosis onset during etanercept treatment," Eur. Neurol. 56:91-93 (2008).*
Abraham, E., et al., "Lenercept (p55 tumor necrosis factor receptor fusion protein) in severe sepsis and early septic . . . ", "Crit. Care Med.", 2001, pp. 503-510, vol. 29, No. 3.
Aggarwal, B., "Signalling pathways of the TNF superfamily: a double-edged sword", "Nature Reviews Immunology", Sep. 2003, pp. 745-756, vol. 3.
Behl, Y., et al., "Diabetes-enhanced tumor necrosis factor-alpha production promotes apoptosis and the loss of retinal microvascular . . . ", "The American Journal of Pathology", May 2008, pp. 1411-1418, vol. 172, No. 5.
Beutler, B., et al., "Identity of tumour necrosis factor and the macrophage-secreted factor cachectin", "Nature", Aug. 1985, pp. 552-554, vol. 316, No. 8.
Carswell, E. A., et al., "An endotoxin-induced serum factor that causes necrosis of tumors", "Proc. Nat. Acad. Sci.", Sep. 1975, pp. 3666-3670, vol. 72, No. 9.
Chan, F., et al., "A role for tumor necrosis factor receptor-2 and receptor-interacting protein in programmed necrosis and antivir . . . ", "The Journal of Biological Chemistry", Dec. 19, 2003, pp. 51613-51621, vol. 278, No. 51.
Chen, P., et al., "Mapping the domain(s) critical for the binding of human tumor necrosis factor-alpha to its two receptors", "The Journal of Biological Chemistry", Feb. 10, 1995, pp. 2874-2878, vol. 270, No. 6.
Corcoran, A., et al., "Characterization of ligand binding by the human p55 tumour-necrosis-factor receptor . . . ", "Eur. J. Biochem.", 1994, pp. 831-840, vol. 223.
Edwards, C., "PEGylated recombinant human soluble tumour necrosis factor receptor type I (r-Hu-sTNF-RI): novel high affinity TNF . . . ", "Ann Rheum Dis", 1999, pp. 173-181, vol. 58.
Edwards, C., et al., "Design of PEGylated soluble tumor necrosis factor receptor type I (PEG sTNF-RI) for chronic inflammatory diseases", "Advanced Drug Delivery Reviews", 2003, pp. 1315-1336, vol. 55.

(Continued)

*Primary Examiner* — Christina Bradley
*Assistant Examiner* — Kristina M Hellman
(74) *Attorney, Agent, or Firm* — Hultquist, PLLC; Steven J. Hultquist; Mary B. Grant

(57) ABSTRACT

The present invention relates to a modified human tumor necrosis factor receptor-1 polypeptide which is capable of binding to a tumor necrosis factor in vivo or ex vivo, or to a fragment thereof. The modified human tumor necrosis factor receptor-1 polypeptide or the fragment thereof according to the present invention exhibit improved binding affinity to the tumor necrosis factor.

18 Claims, 9 Drawing Sheets

(56) References Cited

OTHER PUBLICATIONS

Figure 1:
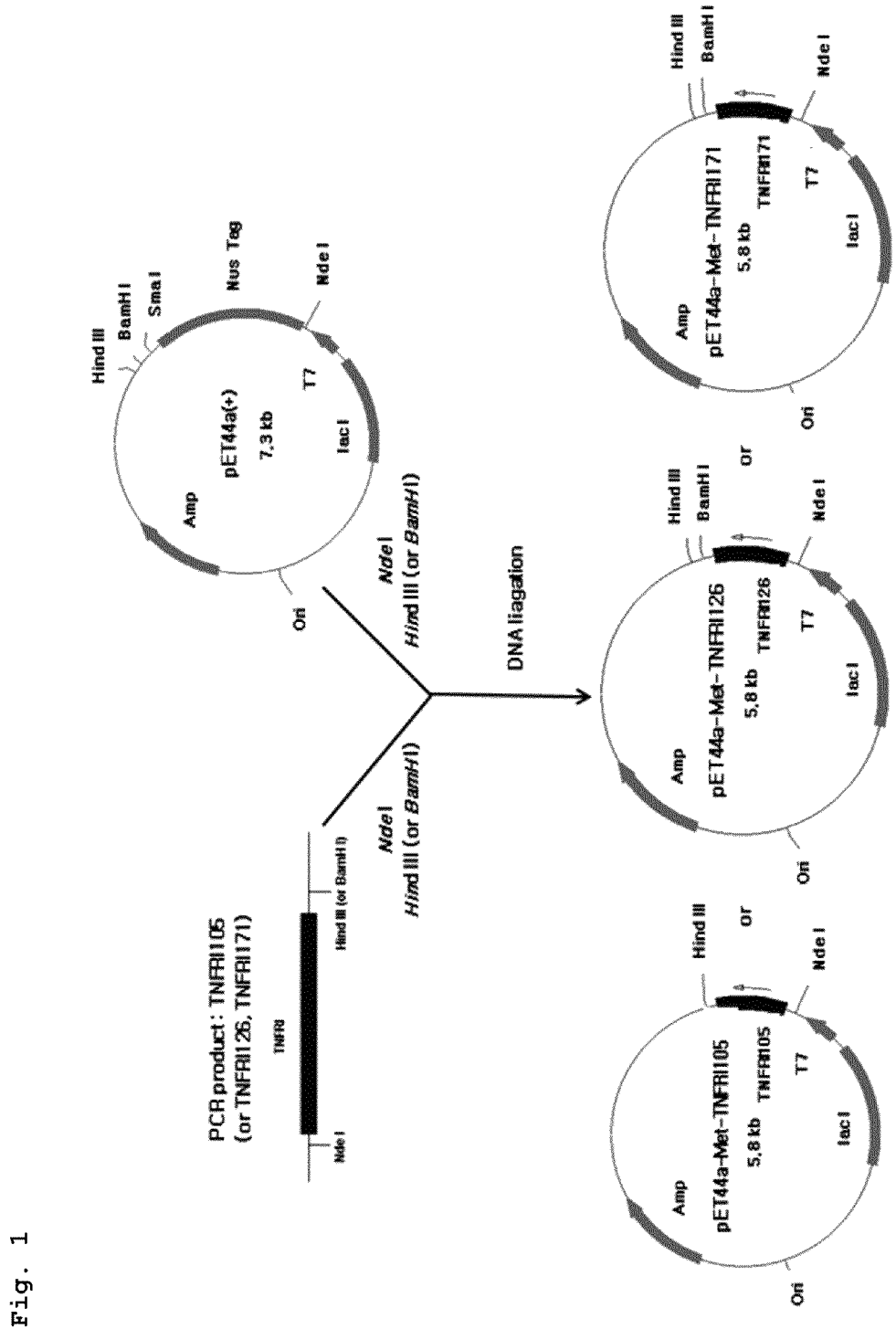

Engelmann, H., et al., "Antibodies to a soluble form of a tumor necrosis factor (TNF) receptor have TNF-like activity", "The Journal of Biological Chemistry", Aug. 25, 1990, pp. 14497-14504, vol. 265, No. 24.

Feldmann, M., et al., "TNF defined as a therapeutic target for rheumatoid arthritis and other autoimmune diseases", "Nature Medicine", Oct. 2003, pp. 1245-1250, vol. 9, No. 10.

Furst, D., et al., "Intravenous human recombinant tumor necrosis factor receptor p55-Fc IgG1: results of a dose-finding study in rheumot . . . ", "Journal of Rheumatology", 2003, pp. 2123-2126, vol. 30.

Kafrouni, M., et al., "The role of TNF-TNFR2 interactions in generation of CTL responses and clearance of hepatic adenovirus infection", "Journal of Leukocyte Biology", Oct. 2003, pp. 564-571, vol. 74.

Kooloos, W., et al., "Potential role of pharmacogenetics in anti-TNF treatment of rheumatoid arthritis and Crohn's disease", "Drug Discovery Today", Feb. 2007, pp. 125-131, vol. 12, No. 3/4.

Old, L., "Tumor necrosis factor (TNF)", "Science", Nov. 8, 1985, pp. 630-632, vol. 230.

Oliff, A., et al., "Tumors secreting human TNF/Cachectin induce cachexia in mice", "Cell", Aug. 14, 1987, pp. 555-563, vol. 50.

Rahman, M., et al., "Modulation of tumor necrosis factor by microbial pathogens", "PLoS Pathogens", 2006, pp. 0066-0077, vol. 2, No. 2.

Rau, R., et al., "Intravenous human recombinant tumor necrosis factor receptor p55-Fc IgG1 fusion protein Ro 45/2081 (Lenercept): a dou . . . ", "The Journal of Rheumatology", 2003, pp. 680-691, vol. 30, No. 4.

Rothe, J., et al., "Mice lacking the tumour necrosis factor receptor 1 are resistant to TNF-mediated toxicity but highly susceptible to . . . ", "Nature", Aug. 26, 1983, pp. 798-802, vol. 364.

Rutgeerts, P., et al., "Optimizing anti-TNF treatment in inflammatory bowel disease", "Gastroenterology", 2004, pp. 1593-1610, vol. 126.

Scallon, B., et al., "Functional comparisons of different tumour necrosis factor receptor/IgG fusion proteins", "Cytokine", Nov. 1995, pp. 759-770, vol. 7, No. 8.

Selby, P., et al., "Endogenous tumour necrosis factor in cancer patients", "Lancet", 1988, p. 483, vol. 1.

Solorzano, C., et al., "Pharmacokinetics, immunogenicity, and efficacy of dimeric TNFR binding proteins in healthy and bacteremic baboon", "Journal of Applied Physiology", 1998, pp. 1119-1130, vol. 84.

Starnes, H., et al., "Tumor necrosis factor and the acute metabolic response to tissue injury in man", "J. Clin. Invest.", Oct. 1988, pp. 1321-1325, vol. 82.

Tartaglia, L., et al., "Ligand passing colon the 75-kDa tumor necrosis factor (TNF receptor recruits TNF for signaling by the 55-kDa TNF rece . . . ", "The Journal of Biological Chemistry", 1993, pp. 18542-18548, vol. 268, No. 25.

Waage, A., et al., "Association between tumour necrosis factor in serum and fatal outcome in patients with meningococcal disease", "Lancet", 1987, pp. 355-357, vol. 1.

Wajant, H., et al., "Tumor necrosis factor signaling", "Cell Death and Differentiation", 2003, pp. 45-65, vol. 10.

Zhou, H., "Clinical Pharmacokinetics of etanercept: a fully humanized soluble recombinant tumor necrosis factor receptor fusion . . . ", "J Clin Pharmacol", 2005, pp. 490-497, vol. 45.

\* cited by examiner

SEQUENCE LISTING

<160> NUMBER OF SEQ ID NOS: 166

<210> SEQ ID NO 1
<211> LENGTH: 455
<212> TYPE: PRT
<213> ORGANISM: Homo sapiens

<400> SEQUENCE: 1

```
Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
    65                  70                  75                  80

Cys Arg Glu Cys Glu Ser Gly Ser Phe Thr Ala Ser Glu Asn His Leu
                85                  90                  95
```

```
Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
        130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
        210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
        450                 455

<210> SEQ ID NO 2
<211> LENGTH: 105
<212> TYPE: PRT
<213> ORGANISM: Homo sapiens
<220> FEATURE:
<221> NAME/KEY: PEPTIDE
<222> LOCATION: (1)..(105)
<223> OTHER INFORMATION: TNFRI105 FRAGMENT
```

<400> SEQUENCE: 2

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ser Glu Asn His Leu Arg His Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 3
<211> LENGTH: 126
<212> TYPE: PRT
<213> ORGANISM: Homo sapiens
<220> FEATURE:
<221> NAME/KEY: PEPTIDE
<222> LOCATION: (1)..(126)
<223> OTHER INFORMATION: TNFRI 126 FRAGMENT

<400> SEQUENCE: 3

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ser Glu Asn His Leu Arg His Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 4
<211> LENGTH: 171
<212> TYPE: PRT
<213> ORGANISM: Homo sapiens
<220> FEATURE:
<221> NAME/KEY: PEPTIDE
<222> LOCATION: (1)..(171)
<223> OTHER INFORMATION: TNFRI 171 FRAGMENT

<400> SEQUENCE: 4

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

```
Phe Thr Ala Ser Glu Asn His Leu Arg His Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 5
<211> LENGTH: 516
<212> TYPE: DNA
<213> ORGANISM: Artificial Sequence
<220> FEATURE:
<223> OTHER INFORMATION: SYNTHETIC TNFRI171 NUCLEIC ACID SEQUENCE

<400> SEQUENCE: 5

```
gatagcgtgt gcccgcaggg taagtatatt catccgcaaa ataactctat ctgttgcaca    60
aagtgtcaca aagggacgta cctgtataat gactgtccgg ggccgggtca ggataccgac   120
tgccgcgagt gcgagagtgg gtcatttaca gcgagtgaga atcatctgcg ccactgcctg   180
agctgttcta agtgtcgtaa agagatgggc caagttgaaa tttcttcatg tacggtagac   240
cgcgatacgg tatgtggttg ccgtaaaaac cagtatcgcc attattggtc agaaaacctg   300
ttccagtgtt ttaattgctc cctgtgtctg aacggcactg tgcatctgtc ctgtcaggag   360
aagcagaata gtttgtac ctgccatgca ggtttctttc taagagaaaa cgagtgtgtc   420
tcctgtagta actgtaagaa aagcctggag tgcacgaagt tgtgcctacc ccagattgag   480
aatgttaagg gcactgagga ctcaggcacc acataa                             516
```

<210> SEQ ID NO 6
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: MET ADDED TNFRI105

<400> SEQUENCE: 6

```
Met Asp Ser Val Cys Pro Gln Gly Lys Tyr Ile His Pro Gln Asn Asn
  1               5                  10                  15

Ser Ile Cys Cys Thr Lys Cys His Lys Gly Thr Tyr Leu Tyr Asn Asp
             20                  25                  30

Cys Pro Gly Pro Gly Gln Asp Thr Asp Cys Arg Glu Cys Glu Ser Gly
         35                  40                  45

Ser Phe Thr Ala Ser Glu Asn His Leu Arg His Cys Leu Ser Cys Ser
     50                  55                  60

Lys Cys Arg Lys Glu Met Gly Gln Val Glu Ile Ser Ser Cys Thr Val
 65                  70                  75                  80
```

```
Asp Arg Asp Thr Val Cys Gly Cys Arg Lys Asn Gln Tyr Arg His Tyr
                85                  90                  95

Trp Ser Glu Asn Leu Phe Gln Cys Phe Asn
            100                 105

<210> SEQ ID NO 7
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: MET ADDED TNFRI126

<400> SEQUENCE: 7

Met Asp Ser Val Cys Pro Gln Gly Lys Tyr Ile His Pro Gln Asn Asn
 1               5                  10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
            35                  40                  45

Ser Phe Thr Ala Ser Glu Asn His Leu Arg His Cys Leu Ser Cys Ser
        50                  55                  60

Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Asn Cys Ser Leu Cys Leu Asn
            100                 105                 110

Gly Thr Val His Leu Ser Cys Gln Glu Lys Gln Asn Thr Val Cys
        115                 120                 125

<210> SEQ ID NO 8
<211> LENGTH: 172
<212> TYPE: PRT
<213> ORGANISM: Homo sapiens
<220> FEATURE:
<221> NAME/KEY: PEPTIDE
<222> LOCATION: (1)..(172)
<223> OTHER INFORMATION: MET ADDED TNFRI171

<400> SEQUENCE: 8

Met Asp Ser Val Cys Pro Gln Gly Lys Tyr Ile His Pro Gln Asn Asn
 1               5                  10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
            35                  40                  45

Ser Phe Thr Ala Ser Glu Asn His Leu Arg His Cys Leu Ser Cys Ser
        50                  55                  60

Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Asn Cys Ser Leu Cys Leu Asn
            100                 105                 110

Gly Thr Val His Leu Ser Cys Gln Glu Lys Gln Asn Thr Val Cys Thr
        115                 120                 125
```

```
Cys His Ala Gly Phe Phe Leu Arg Glu Asn Glu Cys Val Ser Cys Ser
        130                 135                 140

Asn Cys Lys Lys Ser Leu Glu Cys Thr Lys Leu Cys Leu Pro Gln Ile
145                 150                 155                 160

Glu Asn Val Lys Gly Thr Glu Asp Ser Gly Thr Thr
                165                 170

<210> SEQ ID NO 9
<211> LENGTH: 105
<212> TYPE: PRT
<213> ORGANISM: Artificial Sequence
<220> FEATURE:
<223> OTHER INFORMATION: TNFRI105-1

<400> SEQUENCE: 9

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ser Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 10
<211> LENGTH: 105
<212> TYPE: PRT
<213> ORGANISM: Artificial Sequence
<220> FEATURE:
<223> OTHER INFORMATION: TNFRI105-2

<400> SEQUENCE: 10

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 11
<211> LENGTH: 105
<212> TYPE: PRT
<213> ORGANISM: Artificial Sequence
<220> FEATURE:
<223> OTHER INFORMATION: TNFRI105-3
```

```
<400> SEQUENCE: 11

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Gly Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 12
<211> LENGTH: 105
<212> TYPE: PRT
<213> ORGANISM: Artificial Sequence
<220> FEATURE:
<223> OTHER INFORMATION: TNFRI105-4

<400> SEQUENCE: 12

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ala Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 13
<211> LENGTH: 105
<212> TYPE: PRT
<213> ORGANISM: Artificial Sequence
<220> FEATURE:
<223> OTHER INFORMATION: TNFRI105-5

<400> SEQUENCE: 13

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Val Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80
```

```
Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 14
<211> LENGTH: 105
<212> TYPE: PRT
<213> ORGANISM: Artificial Sequence
<220> FEATURE:
<223> OTHER INFORMATION: TNFRI105-6

<400> SEQUENCE: 14

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Leu Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 15
<211> LENGTH: 105
<212> TYPE: PRT
<213> ORGANISM: Artificial Sequence
<220> FEATURE:
<223> OTHER INFORMATION: TNFRI105-7

<400> SEQUENCE: 15

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Pro Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 16
<211> LENGTH: 105
<212> TYPE: PRT
<213> ORGANISM: Artificial Sequence
<220> FEATURE:
<223> OTHER INFORMATION: TNFRI105-8

<400> SEQUENCE: 16

Asp Ser Val Cys Pro Gln Gly Lys Tyr Ile His Pro Gln Asn Asn Ser
```

```
            1               5                  10                 15
Ile Cys Cys Thr Lys Cys His Lys Gly Thr Tyr Leu Tyr Asn Asp Cys
                20                 25                 30

Pro Gly Pro Gly Gln Asp Thr Asp Cys Arg Glu Cys Glu Ser Gly Ser
            35                 40                 45

Phe Thr Ala Phe Glu Asn Phe Leu Pro Ala Cys Leu Ser Cys Ser Lys
        50                 55                 60

Cys Arg Lys Glu Met Gly Gln Val Glu Ile Ser Ser Cys Thr Val Asp
 65              70                 75                 80

Arg Asp Thr Val Cys Gly Cys Arg Lys Asn Gln Tyr Arg His Tyr Trp
                    85                 90                 95

Ser Glu Asn Leu Phe Gln Cys Phe Asn
            100                 105
```

<210> SEQ ID NO 17
<211> LENGTH: 105
<212> TYPE: PRT
<213> ORGANISM: Artificial Sequence
<220> FEATURE:
<223> OTHER INFORMATION: TNFRI105-9

<400> SEQUENCE: 17

```
Asp Ser Val Cys Pro Gln Gly Lys Tyr Ile His Pro Gln Asn Asn Ser
 1               5                  10                 15

Ile Cys Cys Thr Lys Cys His Lys Gly Thr Tyr Leu Tyr Asn Asp Cys
                20                 25                 30

Pro Gly Pro Gly Gln Asp Thr Asp Cys Arg Glu Cys Glu Ser Gly Ser
            35                 40                 45

Phe Thr Ala Met Glu Asn Phe Leu Pro Ala Cys Leu Ser Cys Ser Lys
        50                 55                 60

Cys Arg Lys Glu Met Gly Gln Val Glu Ile Ser Ser Cys Thr Val Asp
 65              70                 75                 80

Arg Asp Thr Val Cys Gly Cys Arg Lys Asn Gln Tyr Arg His Tyr Trp
                    85                 90                 95

Ser Glu Asn Leu Phe Gln Cys Phe Asn
            100                 105
```

<210> SEQ ID NO 18
<211> LENGTH: 105
<212> TYPE: PRT
<213> ORGANISM: Artificial Sequence
<220> FEATURE:
<223> OTHER INFORMATION: TNFRI105-10

<400> SEQUENCE: 18

```
Asp Ser Val Cys Pro Gln Gly Lys Tyr Ile His Pro Gln Asn Asn Ser
 1               5                  10                 15

Ile Cys Cys Thr Lys Cys His Lys Gly Thr Tyr Leu Tyr Asn Asp Cys
                20                 25                 30

Pro Gly Pro Gly Gln Asp Thr Asp Cys Arg Glu Cys Glu Ser Gly Ser
            35                 40                 45

Phe Thr Ala Trp Glu Asn Phe Leu Pro Ala Cys Leu Ser Cys Ser Lys
        50                 55                 60

Cys Arg Lys Glu Met Gly Gln Val Glu Ile Ser Ser Cys Thr Val Asp
 65              70                 75                 80

Arg Asp Thr Val Cys Gly Cys Arg Lys Asn Gln Tyr Arg His Tyr Trp
                    85                 90                 95
```

Ser Glu Asn Leu Phe Gln Cys Phe Asn
            100                 105

<210> SEQ ID NO 19
<211> LENGTH: 105
<212> TYPE: PRT
<213> ORGANISM: Artificial Sequence
<220> FEATURE:
<223> OTHER INFORMATION: TNFRI105-11

<400> SEQUENCE: 19

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Cys Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 20
<211> LENGTH: 105
<212> TYPE: PRT
<213> ORGANISM: Artificial Sequence
<220> FEATURE:
<223> OTHER INFORMATION: TNFRI105-12

<400> SEQUENCE: 20

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Asn Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 21
<211> LENGTH: 105
<212> TYPE: PRT
<213> ORGANISM: Artificial Sequence
<220> FEATURE:
<223> OTHER INFORMATION: TNFRI105-13

<400> SEQUENCE: 21

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys

```
                    20                  25                  30

Pro Gly Pro Gly Gln Asp Thr Asp Cys Arg Glu Cys Glu Ser Gly Ser
            35                  40                  45

Phe Thr Ala Gln Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 22
<211> LENGTH: 105
<212> TYPE: PRT
<213> ORGANISM: Artificial Sequence
<220> FEATURE:
<223> OTHER INFORMATION: TNFRI105-14

<400> SEQUENCE: 22

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Thr Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105

<210> SEQ ID NO 23
<211> LENGTH: 105
<212> TYPE: PRT
<213> ORGANISM: Artificial Sequence
<220> FEATURE:
<223> OTHER INFORMATION: TNFRI105-15

<400> SEQUENCE: 23

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Tyr Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
                100                 105
```

<210> SEQ ID NO 24
<211> LENGTH: 105
<212> TYPE: PRT
<213> ORGANISM: Artificial Sequence
<220> FEATURE:
<223> OTHER INFORMATION: TNFRI105-16

<400> SEQUENCE: 24

```
Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Lys Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105
```

<210> SEQ ID NO 25
<211> LENGTH: 105
<212> TYPE: PRT
<213> ORGANISM: Artificial Sequence
<220> FEATURE:
<223> OTHER INFORMATION: TNFRI105-17

<400> SEQUENCE: 25

```
Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Arg Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105
```

<210> SEQ ID NO 26
<211> LENGTH: 105
<212> TYPE: PRT
<213> ORGANISM: Artificial Sequence
<220> FEATURE:
<223> OTHER INFORMATION: TNFRI105-18

<400> SEQUENCE: 26

```
Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
```

```
                35                  40                  45

Phe Thr Ala His Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 27
<211> LENGTH: 105
<212> TYPE: PRT
<213> ORGANISM: Artificial Sequence
<220> FEATURE:
<223> OTHER INFORMATION: TNFRI105-19

<400> SEQUENCE: 27

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Asp Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 28
<211> LENGTH: 105
<212> TYPE: PRT
<213> ORGANISM: Artificial Sequence
<220> FEATURE:
<223> OTHER INFORMATION: TNFRI105-20

<400> SEQUENCE: 28

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Glu Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 29
<211> LENGTH: 105
```

```
<212> TYPE: PRT
<213> ORGANISM: Artificial Sequence
<220> FEATURE:
<223> OTHER INFORMATION: TNFRI105-21

<400> SEQUENCE: 29

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Glu Asn Phe Leu Pro Gly Cys Leu Ser Cys Ser Lys
        50                  55                  60

Cys Arg Lys Glu Met Gly Gln Val Glu Ile Ser Ser Cys Thr Val Asp
 65                 70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 30
<211> LENGTH: 105
<212> TYPE: PRT
<213> ORGANISM: Artificial Sequence
<220> FEATURE:
<223> OTHER INFORMATION: TNFRI105-22

<400> SEQUENCE: 30

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Gly Cys Leu Ser Cys Ser Lys
        50                  55                  60

Cys Arg Lys Glu Met Gly Gln Val Glu Ile Ser Ser Cys Thr Val Asp
 65                 70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 31
<211> LENGTH: 105
<212> TYPE: PRT
<213> ORGANISM: Artificial Sequence
<220> FEATURE:
<223> OTHER INFORMATION: TNFRI105-23

<400> SEQUENCE: 31

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Leu Ala Cys Leu Ser Cys Ser Lys
```

```
                    50                  55                  60
Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95

Ser Glu Asn Leu Phe Gln Cys Phe Asn
                100                 105

<210> SEQ ID NO 32
<211> LENGTH: 105
<212> TYPE: PRT
<213> ORGANISM: Artificial Sequence
<220> FEATURE:
<223> OTHER INFORMATION: TNFRI105-24

<400> SEQUENCE: 32

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Ile Pro Asn Phe Leu Ile Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95

Ser Glu Asn Leu Phe Gln Cys Phe Asn
                100                 105

<210> SEQ ID NO 33
<211> LENGTH: 105
<212> TYPE: PRT
<213> ORGANISM: Artificial Sequence
<220> FEATURE:
<223> OTHER INFORMATION: TNFRI105-25

<400> SEQUENCE: 33

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Ile Pro Asn Phe Leu Phe Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95

Ser Glu Asn Leu Phe Gln Cys Phe Asn
                100                 105

<210> SEQ ID NO 34
<211> LENGTH: 105
<212> TYPE: PRT
<213> ORGANISM: Artificial Sequence
<220> FEATURE:
```

<223> OTHER INFORMATION: TNFRI105-26

<400> SEQUENCE: 34

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 35
<211> LENGTH: 105
<212> TYPE: PRT
<213> ORGANISM: Artificial Sequence
<220> FEATURE:
<223> OTHER INFORMATION: TNFRI105-27

<400> SEQUENCE: 35

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Leu Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn
            100                 105

<210> SEQ ID NO 36
<211> LENGTH: 105
<212> TYPE: PRT
<213> ORGANISM: Artificial Sequence
<220> FEATURE:
<223> OTHER INFORMATION: TNFRI105-28

<400> SEQUENCE: 36

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Ile Gly Cys Leu Ser Cys Ser Lys
    50                  55                  60

Cys Arg Lys Glu Met Gly Gln Val Glu Ile Ser Ser Cys Thr Val Asp

```
                65                  70                  75                  80
Arg Asp Thr Val Cys Gly Cys Arg Lys Asn Gln Tyr Arg His Tyr Trp
                    85                  90                  95

Ser Glu Asn Leu Phe Gln Cys Phe Asn
                100                 105

<210> SEQ ID NO 37
<211> LENGTH: 105
<212> TYPE: PRT
<213> ORGANISM: Artificial Sequence
<220> FEATURE:
<223> OTHER INFORMATION: TNFRI105-29

<400> SEQUENCE: 37

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Ile Pro Asn Phe Leu Phe Gly Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                     85                  90                  95

Ser Glu Asn Leu Phe Gln Cys Phe Asn
                100                 105

<210> SEQ ID NO 38
<211> LENGTH: 105
<212> TYPE: PRT
<213> ORGANISM: Artificial Sequence
<220> FEATURE:
<223> OTHER INFORMATION: TNFRI105-30

<400> SEQUENCE: 38

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Ile Pro Asn Phe Leu Pro Ala Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                     85                  90                  95

Ser Glu Asn Leu Phe Gln Cys Phe Asn
                100                 105

<210> SEQ ID NO 39
<211> LENGTH: 126
<212> TYPE: PRT
<213> ORGANISM: Artificial Sequence
<220> FEATURE:
<223> OTHER INFORMATION: TNFRI126-1

<400> SEQUENCE: 39
```

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 40
<211> LENGTH: 126
<212> TYPE: PRT
<213> ORGANISM: Artificial Sequence
<220> FEATURE:
<223> OTHER INFORMATION: TNFRI126-2

<400> SEQUENCE: 40

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 41
<211> LENGTH: 126
<212> TYPE: PRT
<213> ORGANISM: Artificial Sequence
<220> FEATURE:
<223> OTHER INFORMATION: TNFRI126-3

<400> SEQUENCE: 41

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Gly Glu Asn Phe Leu Pro Ala Cys Leu Ser Cys Ser Lys

```
                    50                  55                  60
Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                    100                 105                 110

Thr Val His Leu Ser Cys Gln Glu Lys Gln Asn Thr Val Cys
            115                 120                 125
```

<210> SEQ ID NO 42
<211> LENGTH: 126
<212> TYPE: PRT
<213> ORGANISM: Artificial Sequence
<220> FEATURE:
<223> OTHER INFORMATION: TNFRI126-4

<400> SEQUENCE: 42

```
Asp Ser Val Cys Pro Gln Gly Lys Tyr Ile His Pro Gln Asn Asn Ser
 1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ala Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                    100                 105                 110

Thr Val His Leu Ser Cys Gln Glu Lys Gln Asn Thr Val Cys
            115                 120                 125
```

<210> SEQ ID NO 43
<211> LENGTH: 126
<212> TYPE: PRT
<213> ORGANISM: Artificial Sequence
<220> FEATURE:
<223> OTHER INFORMATION: TNFRI126-5

<400> SEQUENCE: 43

```
Asp Ser Val Cys Pro Gln Gly Lys Tyr Ile His Pro Gln Asn Asn Ser
 1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Val Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                    100                 105                 110
```

```
Thr Val His Leu Ser Cys Gln Glu Lys Gln Asn Thr Val Cys
        115                 120                 125

<210> SEQ ID NO 44
<211> LENGTH: 126
<212> TYPE: PRT
<213> ORGANISM: Artificial Sequence
<220> FEATURE:
<223> OTHER INFORMATION: TNFRI126-6

<400> SEQUENCE: 44

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Leu Glu Asn Phe Leu Pro Ala Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
        115                 120                 125

<210> SEQ ID NO 45
<211> LENGTH: 126
<212> TYPE: PRT
<213> ORGANISM: Artificial Sequence
<220> FEATURE:
<223> OTHER INFORMATION: TNFRI126-7

<400> SEQUENCE: 45

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Pro Glu Asn Phe Leu Pro Ala Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
        115                 120                 125

<210> SEQ ID NO 46
<211> LENGTH: 126
<212> TYPE: PRT
<213> ORGANISM: Artificial Sequence
<220> FEATURE:
<223> OTHER INFORMATION: TNFRI126-8
```

<400> SEQUENCE: 46

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Phe Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 47
<211> LENGTH: 126
<212> TYPE: PRT
<213> ORGANISM: Artificial Sequence
<220> FEATURE:
<223> OTHER INFORMATION: TNFRI126-9

<400> SEQUENCE: 47

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 48
<211> LENGTH: 126
<212> TYPE: PRT
<213> ORGANISM: Artificial Sequence
<220> FEATURE:
<223> OTHER INFORMATION: TNFRI126-10

<400> SEQUENCE: 48

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Trp Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 49
<211> LENGTH: 126
<212> TYPE: PRT
<213> ORGANISM: Artificial Sequence
<220> FEATURE:
<223> OTHER INFORMATION: TNFRI126-11

<400> SEQUENCE: 49

Asp Ser Val Cys Pro Gln Gly Lys Tyr Ile His Pro Gln Asn Asn Ser
 1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Cys Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 50
<211> LENGTH: 126
<212> TYPE: PRT
<213> ORGANISM: Artificial Sequence
<220> FEATURE:
<223> OTHER INFORMATION: TNFRI126-12

<400> SEQUENCE: 50

Asp Ser Val Cys Pro Gln Gly Lys Tyr Ile His Pro Gln Asn Asn Ser
 1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Asn Glu Asn Phe Leu Pro Ala Cys Leu Ser Cys Ser Lys
            50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

```
Thr Val His Leu Ser Cys Gln Glu Lys Gln Asn Thr Val Cys
        115                 120                 125

<210> SEQ ID NO 51
<211> LENGTH: 126
<212> TYPE: PRT
<213> ORGANISM: Artificial Sequence
<220> FEATURE:
<223> OTHER INFORMATION: TNFRI126-13

<400> SEQUENCE: 51

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Gln Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 52
<211> LENGTH: 126
<212> TYPE: PRT
<213> ORGANISM: Artificial Sequence
<220> FEATURE:
<223> OTHER INFORMATION: TNFRI126-14

<400> SEQUENCE: 52

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Thr Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 53
<211> LENGTH: 126
<212> TYPE: PRT
<213> ORGANISM: Artificial Sequence
<220> FEATURE:
<223> OTHER INFORMATION: TNFRI126-15
```

<400> SEQUENCE: 53

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Tyr Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65              70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 54
<211> LENGTH: 126
<212> TYPE: PRT
<213> ORGANISM: Artificial Sequence
<220> FEATURE:
<223> OTHER INFORMATION: TNFRI126-16

<400> SEQUENCE: 54

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Lys Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65              70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 55
<211> LENGTH: 126
<212> TYPE: PRT
<213> ORGANISM: Artificial Sequence
<220> FEATURE:
<223> OTHER INFORMATION: TNFRI126-17

<400> SEQUENCE: 55

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

```
Phe Thr Ala Arg Glu Asn Phe Leu Pro Ala Cys Leu Ser Cys Ser Lys
             50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
            115                 120                 125

<210> SEQ ID NO 56
<211> LENGTH: 126
<212> TYPE: PRT
<213> ORGANISM: Artificial Sequence
<220> FEATURE:
<223> OTHER INFORMATION: TNFRI126-18

<400> SEQUENCE: 56

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala His Glu Asn Phe Leu Pro Ala Cys Leu Ser Cys Ser Lys
             50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
            115                 120                 125

<210> SEQ ID NO 57
<211> LENGTH: 126
<212> TYPE: PRT
<213> ORGANISM: Artificial Sequence
<220> FEATURE:
<223> OTHER INFORMATION: TNFRI126-19

<400> SEQUENCE: 57

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Asp Glu Asn Phe Leu Pro Ala Cys Leu Ser Cys Ser Lys
             50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
```

```
                        100                 105                 110
Thr Val His Leu Ser Cys Gln Glu Lys Gln Asn Thr Val Cys
        115                 120                 125
```

<210> SEQ ID NO 58
<211> LENGTH: 126
<212> TYPE: PRT
<213> ORGANISM: Artificial Sequence
<220> FEATURE:
<223> OTHER INFORMATION: TNFRI126-20

<400> SEQUENCE: 58

```
Asp Ser Val Cys Pro Gln Gly Lys Tyr Ile His Pro Gln Asn Asn Ser
1               5                   10                  15
Ile Cys Cys Thr Lys Cys His Lys Gly Thr Tyr Leu Tyr Asn Asp Cys
                20                  25                  30
Pro Gly Pro Gly Gln Asp Thr Asp Cys Arg Glu Cys Glu Ser Gly Ser
            35                  40                  45
Phe Thr Ala Glu Glu Asn Phe Leu Pro Ala Cys Leu Ser Cys Ser Lys
        50                  55                  60
Cys Arg Lys Glu Met Gly Gln Val Glu Ile Ser Ser Cys Thr Val Asp
65                  70                  75                  80
Arg Asp Thr Val Cys Gly Cys Arg Lys Asn Gln Tyr Arg His Tyr Trp
                85                  90                  95
Ser Glu Asn Leu Phe Gln Cys Phe Asn Cys Ser Leu Cys Leu Asn Gly
                100                 105                 110
Thr Val His Leu Ser Cys Gln Glu Lys Gln Asn Thr Val Cys
        115                 120                 125
```

<210> SEQ ID NO 59
<211> LENGTH: 126
<212> TYPE: PRT
<213> ORGANISM: Artificial Sequence
<220> FEATURE:
<223> OTHER INFORMATION: TNFRI126-21

<400> SEQUENCE: 59

```
Asp Ser Val Cys Pro Gln Gly Lys Tyr Ile His Pro Gln Asn Asn Ser
1               5                   10                  15
Ile Cys Cys Thr Lys Cys His Lys Gly Thr Tyr Leu Tyr Asn Asp Cys
                20                  25                  30
Pro Gly Pro Gly Gln Asp Thr Asp Cys Arg Glu Cys Glu Ser Gly Ser
            35                  40                  45
Phe Thr Ala Ile Glu Asn Phe Leu Pro Gly Cys Leu Ser Cys Ser Lys
        50                  55                  60
Cys Arg Lys Glu Met Gly Gln Val Glu Ile Ser Ser Cys Thr Val Asp
65                  70                  75                  80
Arg Asp Thr Val Cys Gly Cys Arg Lys Asn Gln Tyr Arg His Tyr Trp
                85                  90                  95
Ser Glu Asn Leu Phe Gln Cys Phe Asn Cys Ser Leu Cys Leu Asn Gly
                100                 105                 110
Thr Val His Leu Ser Cys Gln Glu Lys Gln Asn Thr Val Cys
        115                 120                 125
```

<210> SEQ ID NO 60
<211> LENGTH: 126
<212> TYPE: PRT
<213> ORGANISM: Artificial Sequence
<220> FEATURE:

<223> OTHER INFORMATION: TNFRI126-22

<400> SEQUENCE: 60

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Met Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 61
<211> LENGTH: 126
<212> TYPE: PRT
<213> ORGANISM: Artificial Sequence
<220> FEATURE:
<223> OTHER INFORMATION: TNFRI126-23

<400> SEQUENCE: 61

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Leu Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 62
<211> LENGTH: 126
<212> TYPE: PRT
<213> ORGANISM: Artificial Sequence
<220> FEATURE:
<223> OTHER INFORMATION: TNFRI126-24

<400> SEQUENCE: 62

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser

```
                    35                  40                  45

Phe Thr Ala Ile Pro Asn Phe Leu Ile Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 63
<211> LENGTH: 126
<212> TYPE: PRT
<213> ORGANISM: Artificial Sequence
<220> FEATURE:
<223> OTHER INFORMATION: TNFRI126-25

<400> SEQUENCE: 63

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Phe Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys
            115                 120                 125

<210> SEQ ID NO 64
<211> LENGTH: 126
<212> TYPE: PRT
<213> ORGANISM: Artificial Sequence
<220> FEATURE:
<223> OTHER INFORMATION: TNFRI126-26

<400> SEQUENCE: 64

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Pro Gly Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                    85                  90                  95
```

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 65
<211> LENGTH: 126
<212> TYPE: PRT
<213> ORGANISM: Artificial Sequence
<220> FEATURE:
<223> OTHER INFORMATION: TNFRI126-27

<400> SEQUENCE: 65

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Leu Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 66
<211> LENGTH: 126
<212> TYPE: PRT
<213> ORGANISM: Artificial Sequence
<220> FEATURE:
<223> OTHER INFORMATION: TNFRI126-28

<400> SEQUENCE: 66

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Pro Asn Phe Leu Ile Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 67
<211> LENGTH: 126
<212> TYPE: PRT
<213> ORGANISM: Artificial Sequence

```
<220> FEATURE:
<223> OTHER INFORMATION: TNFRI126-29

<400> SEQUENCE: 67

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Phe Gly Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 68
<211> LENGTH: 126
<212> TYPE: PRT
<213> ORGANISM: Artificial Sequence
<220> FEATURE:
<223> OTHER INFORMATION: TNFRI126-30

<400> SEQUENCE: 68

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys
        115                 120                 125

<210> SEQ ID NO 69
<211> LENGTH: 171
<212> TYPE: PRT
<213> ORGANISM: Artificial Sequence
<220> FEATURE:
<223> OTHER INFORMATION: TNFRI171-1

<400> SEQUENCE: 69

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30
```

```
Pro Gly Pro Gly Gln Asp Thr Asp Cys Arg Glu Cys Glu Ser Gly Ser
        35                  40                  45

Phe Thr Ala Ser Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 70
<211> LENGTH: 171
<212> TYPE: PRT
<213> ORGANISM: Artificial Sequence
<220> FEATURE:
<223> OTHER INFORMATION: TNFRI171-2

<400> SEQUENCE: 70

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 71
<211> LENGTH: 171
<212> TYPE: PRT
<213> ORGANISM: Artificial Sequence
<220> FEATURE:
<223> OTHER INFORMATION: TNFRI171-3

<400> SEQUENCE: 71
```

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
            35                  40                  45

Phe Thr Ala Gly Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 72
<211> LENGTH: 171
<212> TYPE: PRT
<213> ORGANISM: Artificial Sequence
<220> FEATURE:
<223> OTHER INFORMATION: TNFRI171-4

<400> SEQUENCE: 72

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
            35                  40                  45

Phe Thr Ala Ala Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 73

<211> LENGTH: 171
<212> TYPE: PRT
<213> ORGANISM: Artificial Sequence
<220> FEATURE:
<223> OTHER INFORMATION: TNFRI171-5

<400> SEQUENCE: 73

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Val Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 74
<211> LENGTH: 171
<212> TYPE: PRT
<213> ORGANISM: Artificial Sequence
<220> FEATURE:
<223> OTHER INFORMATION: TNFRI171-6

<400> SEQUENCE: 74

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Leu Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu

```
145                 150                 155                 160
Asn Val Lys Gly Thr Glu Asp Ser Gly Thr Thr
                165                 170

<210> SEQ ID NO 75
<211> LENGTH: 171
<212> TYPE: PRT
<213> ORGANISM: Artificial Sequence
<220> FEATURE:
<223> OTHER INFORMATION: TNFRI171-7

<400> SEQUENCE: 75

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Pro Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
             115                 120                 125

His Ala Gly Phe Phe Leu Arg Glu Asn Glu Cys Val Ser Cys Ser Asn
130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 76
<211> LENGTH: 171
<212> TYPE: PRT
<213> ORGANISM: Artificial Sequence
<220> FEATURE:
<223> OTHER INFORMATION: TNFRI171-8

<400> SEQUENCE: 76

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
             35                  40                  45

Phe Thr Ala Phe Glu Asn Phe Leu Pro Ala Cys Leu Ser Cys Ser Lys
 50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110
```

```
Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 77
<211> LENGTH: 171
<212> TYPE: PRT
<213> ORGANISM: Artificial Sequence
<220> FEATURE:
<223> OTHER INFORMATION: TNFRI171-9

<400> SEQUENCE: 77

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 78
<211> LENGTH: 171
<212> TYPE: PRT
<213> ORGANISM: Artificial Sequence
<220> FEATURE:
<223> OTHER INFORMATION: TNFRI171-10

<400> SEQUENCE: 78

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Trp Glu Asn Phe Leu Pro Ala Cys Leu Ser Cys Ser Lys
        50                  55                  60

Cys Arg Lys Glu Met Gly Gln Val Glu Ile Ser Ser Cys Thr Val Asp
65                  70                  75                  80
```

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 79
<211> LENGTH: 171
<212> TYPE: PRT
<213> ORGANISM: Artificial Sequence
<220> FEATURE:
<223> OTHER INFORMATION: TNFRI171-11

<400> SEQUENCE: 79

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Cys Glu Asn Phe Leu Pro Ala Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 80
<211> LENGTH: 171
<212> TYPE: PRT
<213> ORGANISM: Artificial Sequence
<220> FEATURE:
<223> OTHER INFORMATION: TNFRI171-12

<400> SEQUENCE: 80

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser

```
                35                  40                  45
Phe Thr Ala Asn Glu Asn Phe Leu Pro Ala Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 81
<211> LENGTH: 171
<212> TYPE: PRT
<213> ORGANISM: Artificial Sequence
<220> FEATURE:
<223> OTHER INFORMATION: TNFRI171-13

<400> SEQUENCE: 81

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
            35                  40                  45

Phe Thr Ala Gln Glu Asn Phe Leu Pro Ala Cys Leu Ser Cys Ser Lys
         50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 82
<211> LENGTH: 171
<212> TYPE: PRT
<213> ORGANISM: Artificial Sequence
<220> FEATURE:
<223> OTHER INFORMATION: TNFRI171-14

<400> SEQUENCE: 82
```

-continued

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Thr Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65              70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145             150                 155                 160

Asn Val Lys Gly Thr Glu Asp Ser Gly Thr Thr
                165                 170
```

<210> SEQ ID NO 83
<211> LENGTH: 171
<212> TYPE: PRT
<213> ORGANISM: Artificial Sequence
<220> FEATURE:
<223> OTHER INFORMATION: TNFRI171-15

<400> SEQUENCE: 83

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Tyr Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65              70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145             150                 155                 160

Asn Val Lys Gly Thr Glu Asp Ser Gly Thr Thr
                165                 170
```

<210> SEQ ID NO 84
<211> LENGTH: 171

```
<212> TYPE: PRT
<213> ORGANISM: Artificial Sequence
<220> FEATURE:
<223> OTHER INFORMATION: TNFRI171-16

<400> SEQUENCE: 84

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Lys Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 85
<211> LENGTH: 171
<212> TYPE: PRT
<213> ORGANISM: Artificial Sequence
<220> FEATURE:
<223> OTHER INFORMATION: TNFRI171-17

<400> SEQUENCE: 85

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Arg Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160
```

Asn Val Lys Gly Thr Glu Asp Ser Gly Thr Thr
            165                 170

<210> SEQ ID NO 86
<211> LENGTH: 171
<212> TYPE: PRT
<213> ORGANISM: Artificial Sequence
<220> FEATURE:
<223> OTHER INFORMATION: TNFRI171-18

<400> SEQUENCE: 86

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala His Glu Asn Phe Leu Pro Ala Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
            165                 170

<210> SEQ ID NO 87
<211> LENGTH: 171
<212> TYPE: PRT
<213> ORGANISM: Artificial Sequence
<220> FEATURE:
<223> OTHER INFORMATION: TNFRI171-19

<400> SEQUENCE: 87

Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Asp Glu Asn Phe Leu Pro Ala Cys Leu Ser Cys Ser Lys
     50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 88
<211> LENGTH: 171
<212> TYPE: PRT
<213> ORGANISM: Artificial Sequence
<220> FEATURE:
<223> OTHER INFORMATION: TNFRI171-20

<400> SEQUENCE: 88

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Glu Glu Asn Phe Leu Pro Ala Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 89
<211> LENGTH: 171
<212> TYPE: PRT
<213> ORGANISM: Artificial Sequence
<220> FEATURE:
<223> OTHER INFORMATION: TNFRI171-21

<400> SEQUENCE: 89

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ile Glu Asn Phe Leu Pro Gly Cys Leu Ser Cys Ser Lys
    50                  55                  60

Cys Arg Lys Glu Met Gly Gln Val Glu Ile Ser Ser Cys Thr Val Asp
65                  70                  75                  80

```
Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 90
<211> LENGTH: 171
<212> TYPE: PRT
<213> ORGANISM: Artificial Sequence
<220> FEATURE:
<223> OTHER INFORMATION: TNFRI171-22

<400> SEQUENCE: 90

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Met Glu Asn Phe Leu Pro Gly Cys Leu Ser Cys Ser Lys
        50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170
```

<210> SEQ ID NO 91
<211> LENGTH: 171
<212> TYPE: PRT
<213> ORGANISM: Artificial Sequence
<220> FEATURE:
<223> OTHER INFORMATION: TNFRI171-23

<400> SEQUENCE: 91

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45
```

```
Phe Thr Ala Ile Pro Asn Phe Leu Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 92
<211> LENGTH: 171
<212> TYPE: PRT
<213> ORGANISM: Artificial Sequence
<220> FEATURE:
<223> OTHER INFORMATION: TNFRI171-24

<400> SEQUENCE: 92

Asp Ser Val Cys Pro Gln Gly Lys Tyr Ile His Pro Gln Asn Asn Ser
 1                5                  10                  15

Ile Cys Cys Thr Lys Cys His Lys Gly Thr Tyr Leu Tyr Asn Asp Cys
                 20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Ile Ala Cys Leu Ser Cys Ser Lys
        50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 93
<211> LENGTH: 171
<212> TYPE: PRT
<213> ORGANISM: Artificial Sequence
<220> FEATURE:
<223> OTHER INFORMATION: TNFRI171-25

<400> SEQUENCE: 93

Asp Ser Val Cys Pro Gln Gly Lys Tyr Ile His Pro Gln Asn Asn Ser
```

```
                1               5                   10                  15
            Ile Cys Cys Thr Lys Cys His Lys Gly Thr Tyr Leu Tyr Asn Asp Cys
                                20                  25                  30

Pro Gly Pro Gly Gln Asp Thr Asp Cys Arg Glu Cys Glu Ser Gly Ser
                        35                  40                  45

Phe Thr Ala Ile Pro Asn Phe Leu Phe Ala Cys Leu Ser Cys Ser Lys
                    50                  55                  60

Cys Arg Lys Glu Met Gly Gln Val Glu Ile Ser Ser Cys Thr Val Asp
            65                  70                  75                  80

Arg Asp Thr Val Cys Gly Cys Arg Lys Asn Gln Tyr Arg His Tyr Trp
                                85                  90                  95

Ser Glu Asn Leu Phe Gln Cys Phe Asn Cys Ser Leu Cys Leu Asn Gly
                            100                 105                 110

Thr Val His Leu Ser Cys Gln Glu Lys Gln Asn Thr Val Cys Thr Cys
                        115                 120                 125

His Ala Gly Phe Phe Leu Arg Glu Asn Glu Cys Val Ser Cys Ser Asn
                    130                 135                 140

Cys Lys Lys Ser Leu Glu Cys Thr Lys Leu Cys Leu Pro Gln Ile Glu
            145                 150                 155                 160

Asn Val Lys Gly Thr Glu Asp Ser Gly Thr Thr
                            165                 170

<210> SEQ ID NO 94
<211> LENGTH: 171
<212> TYPE: PRT
<213> ORGANISM: Artificial Sequence
<220> FEATURE:
<223> OTHER INFORMATION: TNFRI171-26

<400> SEQUENCE: 94

Asp Ser Val Cys Pro Gln Gly Lys Tyr Ile His Pro Gln Asn Asn Ser
            1               5                   10                  15

Ile Cys Cys Thr Lys Cys His Lys Gly Thr Tyr Leu Tyr Asn Asp Cys
                                20                  25                  30

Pro Gly Pro Gly Gln Asp Thr Asp Cys Arg Glu Cys Glu Ser Gly Ser
                        35                  40                  45

Phe Thr Ala Ile Pro Asn Phe Leu Pro Gly Cys Leu Ser Cys Ser Lys
                    50                  55                  60

Cys Arg Lys Glu Met Gly Gln Val Glu Ile Ser Ser Cys Thr Val Asp
            65                  70                  75                  80

Arg Asp Thr Val Cys Gly Cys Arg Lys Asn Gln Tyr Arg His Tyr Trp
                                85                  90                  95

Ser Glu Asn Leu Phe Gln Cys Phe Asn Cys Ser Leu Cys Leu Asn Gly
                            100                 105                 110

Thr Val His Leu Ser Cys Gln Glu Lys Gln Asn Thr Val Cys Thr Cys
                        115                 120                 125

His Ala Gly Phe Phe Leu Arg Glu Asn Glu Cys Val Ser Cys Ser Asn
                    130                 135                 140

Cys Lys Lys Ser Leu Glu Cys Thr Lys Leu Cys Leu Pro Gln Ile Glu
            145                 150                 155                 160

Asn Val Lys Gly Thr Glu Asp Ser Gly Thr Thr
                            165                 170

<210> SEQ ID NO 95
<211> LENGTH: 171
<212> TYPE: PRT
```

```
<213> ORGANISM: Artificial Sequence
<220> FEATURE:
<223> OTHER INFORMATION: TNFRI171-27

<400> SEQUENCE: 95

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Leu Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 96
<211> LENGTH: 171
<212> TYPE: PRT
<213> ORGANISM: Artificial Sequence
<220> FEATURE:
<223> OTHER INFORMATION: TNFRI171-28

<400> SEQUENCE: 96

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Ile Gly Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
                115                 120                 125

His Ala Gly Phe Phe Leu Arg Glu Asn Glu Cys Val Ser Cys Ser Asn
            130                 135                 140

Cys Lys Lys Ser Leu Glu Cys Thr Lys Leu Cys Leu Pro Gln Ile Glu
145                 150                 155                 160
```

Asn Val Lys Gly Thr Glu Asp Ser Gly Thr Thr
              165                 170

<210> SEQ ID NO 97
<211> LENGTH: 171
<212> TYPE: PRT
<213> ORGANISM: Artificial Sequence
<220> FEATURE:
<223> OTHER INFORMATION: TNFRI171-29

<400> SEQUENCE: 97

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Phe Gly Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
              165                 170

<210> SEQ ID NO 98
<211> LENGTH: 171
<212> TYPE: PRT
<213> ORGANISM: Artificial Sequence
<220> FEATURE:
<223> OTHER INFORMATION: TNFRI171-30

<400> SEQUENCE: 98

Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ile Pro Asn Phe Leu Pro Ala Cys Leu Ser Cys Ser Lys
    50                  55                  60

Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
            130                 135                 140
Cys Lys Lys Ser Leu Glu Cys Thr Lys Leu Cys Leu Pro Gln Ile Glu
145                 150                 155                 160
Asn Val Lys Gly Thr Glu Asp Ser Gly Thr Thr
                165                 170

<210> SEQ ID NO 99
<211> LENGTH: 58
<212> TYPE: DNA
<213> ORGANISM: Artificial Sequence
<220> FEATURE:
<223> OTHER INFORMATION: Primer for mutant No. #30

<400> SEQUENCE: 99
gagtgggtca tttacagcga ttccgaattt tctgccggcg tgcctgagct gttctaag       58

<210> SEQ ID NO 100
<211> LENGTH: 58
<212> TYPE: DNA
<213> ORGANISM: Artificial Sequence
<220> FEATURE:
<223> OTHER INFORMATION: Primer for mutant No. #30

<400> SEQUENCE: 100
cttagaacag ctcaggcacg ccggcagaaa attcggaatc gctgtaaatg acccactc       58

<210> SEQ ID NO 101
<211> LENGTH: 50
<212> TYPE: DNA
<213> ORGANISM: Artificial Sequence
<220> FEATURE:
<223> OTHER INFORMATION: Primer for mutant No. #1

<400> SEQUENCE: 101
catttacagc gagtgagaat ttctgcgcgc cgtgcctgag ctgttctaag                 50

<210> SEQ ID NO 102
<211> LENGTH: 50
<212> TYPE: DNA
<213> ORGANISM: Artificial Sequence
<220> FEATURE:
<223> OTHER INFORMATION: Primer for mutant No. #1

<400> SEQUENCE: 102
cttagaacag ctcaggcacg cgcgcagaaa attctcactc gctgtaaatg                 50

<210> SEQ ID NO 103
<211> LENGTH: 34
<212> TYPE: DNA
<213> ORGANISM: Artificial Sequence
<220> FEATURE:
<223> OTHER INFORMATION: Primer for mutant No. #1

<400> SEQUENCE: 103
gagtgagaat tttctgccgg cgtgcctgag ctgt                                  34

<210> SEQ ID NO 104
<211> LENGTH: 34
<212> TYPE: DNA
<213> ORGANISM: Artificial Sequence
<220> FEATURE:
<223> OTHER INFORMATION: Primer for mutant No. #1

<400> SEQUENCE: 104

-continued acagctcagg cacgccggca gaaaattctc actc    34

<210> SEQ ID NO 105
<211> LENGTH: 33
<212> TYPE: DNA
<213> ORGANISM: Artificial Sequence
<220> FEATURE:
<223> OTHER INFORMATION: Primer for mutant No. #2

<400> SEQUENCE: 105
gtcatttaca gcgattgaga attttctgcc ggc    33

<210> SEQ ID NO 106
<211> LENGTH: 33
<212> TYPE: DNA
<213> ORGANISM: Artificial Sequence
<220> FEATURE:
<223> OTHER INFORMATION: Primer for mutant No. #2

<400> SEQUENCE: 106
gccggcagaa aattctcaat cgctgtaaat gac    33

<210> SEQ ID NO 107
<211> LENGTH: 31
<212> TYPE: DNA
<213> ORGANISM: Artificial Sequence
<220> FEATURE:
<223> OTHER INFORMATION: Primer for mutant No. #3

<400> SEQUENCE: 107
gggtcattta cagcggggga aattttctg c    31

<210> SEQ ID NO 108
<211> LENGTH: 31
<212> TYPE: DNA
<213> ORGANISM: Artificial Sequence
<220> FEATURE:
<223> OTHER INFORMATION: Primer for mutant No. #3

<400> SEQUENCE: 108
gcagaaaatt ctcccccgct gtaaatgacc c    31

<210> SEQ ID NO 109
<211> LENGTH: 31
<212> TYPE: DNA
<213> ORGANISM: Artificial Sequence
<220> FEATURE:
<223> OTHER INFORMATION: Primer for mutant No. #4

<400> SEQUENCE: 109
gggtcattta cagcggcgga aattttctg c    31

<210> SEQ ID NO 110
<211> LENGTH: 31
<212> TYPE: DNA
<213> ORGANISM: Artificial Sequence
<220> FEATURE:
<223> OTHER INFORMATION: Primer for mutant No. #4

<400> SEQUENCE: 110
gcagaaaatt ctccgccgct gtaaatgacc c    31

<210> SEQ ID NO 111
<211> LENGTH: 31
<212> TYPE: DNA

```
<213> ORGANISM: Artificial Sequence
<220> FEATURE:
<223> OTHER INFORMATION: Primer for mutant No. #5

<400> SEQUENCE: 111
gggtcattta cagcggttga gaattttctg c                                31

<210> SEQ ID NO 112
<211> LENGTH: 31
<212> TYPE: DNA
<213> ORGANISM: Artificial Sequence
<220> FEATURE:
<223> OTHER INFORMATION: Primer for mutant No. #5

<400> SEQUENCE: 112
gcagaaaatt ctcaaccgct gtaaatgacc c                                31

<210> SEQ ID NO 113
<211> LENGTH: 31
<212> TYPE: DNA
<213> ORGANISM: Artificial Sequence
<220> FEATURE:
<223> OTHER INFORMATION: Primer for mutant No. #6

<400> SEQUENCE: 113
gggtcattta cagcgctgga gaattttctg c                                31

<210> SEQ ID NO 114
<211> LENGTH: 31
<212> TYPE: DNA
<213> ORGANISM: Artificial Sequence
<220> FEATURE:
<223> OTHER INFORMATION: Primer for mutant No. #6

<400> SEQUENCE: 114
gcagaaaatt ctccagcgct gtaaatgacc c                                31

<210> SEQ ID NO 115
<211> LENGTH: 31
<212> TYPE: DNA
<213> ORGANISM: Artificial Sequence
<220> FEATURE:
<223> OTHER INFORMATION: Primer for mutant No. #7

<400> SEQUENCE: 115
gggtcattta cagcgccgga gaattttctg c                                31

<210> SEQ ID NO 116
<211> LENGTH: 31
<212> TYPE: DNA
<213> ORGANISM: Artificial Sequence
<220> FEATURE:
<223> OTHER INFORMATION: Primer for mutant No. #7

<400> SEQUENCE: 116
gcagaaaatt ctccggcgct gtaaatgacc c                                31

<210> SEQ ID NO 117
<211> LENGTH: 31
<212> TYPE: DNA
<213> ORGANISM: Artificial Sequence
<220> FEATURE:
<223> OTHER INFORMATION: Primer for mutant No. #8

<400> SEQUENCE: 117
gggtcattta cagcgtttga gaattttctg c                                31
```

<210> SEQ ID NO 118
<211> LENGTH: 31
<212> TYPE: DNA
<213> ORGANISM: Artificial Sequence
<220> FEATURE:
<223> OTHER INFORMATION: Primer for mutant No. #8

<400> SEQUENCE: 118
gcagaaaatt ctcaaacgct gtaaatgacc c                               31

<210> SEQ ID NO 119
<211> LENGTH: 31
<212> TYPE: DNA
<213> ORGANISM: Artificial Sequence
<220> FEATURE:
<223> OTHER INFORMATION: Primer for mutant No. #9

<400> SEQUENCE: 119
gggtcattta cagcgatgga gaattttctg c                               31

<210> SEQ ID NO 120
<211> LENGTH: 31
<212> TYPE: DNA
<213> ORGANISM: Artificial Sequence
<220> FEATURE:
<223> OTHER INFORMATION: Primer for mutant No. #9

<400> SEQUENCE: 120
gcagaaaatt ctccatcgct gtaaatgacc c                               31

<210> SEQ ID NO 121
<211> LENGTH: 31
<212> TYPE: DNA
<213> ORGANISM: Artificial Sequence
<220> FEATURE:
<223> OTHER INFORMATION: Primer for mutant No. #10

<400> SEQUENCE: 121
gggtcattta cagcgtggga gaattttctg c                               31

<210> SEQ ID NO 122
<211> LENGTH: 31
<212> TYPE: DNA
<213> ORGANISM: Artificial Sequence
<220> FEATURE:
<223> OTHER INFORMATION: Primer for mutant No. #10

<400> SEQUENCE: 122
gcagaaaatt ctcccacgct gtaaatgacc c                               31

<210> SEQ ID NO 123
<211> LENGTH: 31
<212> TYPE: DNA
<213> ORGANISM: Artificial Sequence
<220> FEATURE:
<223> OTHER INFORMATION: Primer for mutant No. #11

<400> SEQUENCE: 123
gggtcattta cagcgtgcga gaattttctg c                               31

<210> SEQ ID NO 124
<211> LENGTH: 31
<212> TYPE: DNA
<213> ORGANISM: Artificial Sequence
<220> FEATURE:

<223> OTHER INFORMATION: Primer for mutant No. #11

<400> SEQUENCE: 124
gcagaaaatt ctcgcacgct gtaaatgacc c                           31

<210> SEQ ID NO 125
<211> LENGTH: 31
<212> TYPE: DNA
<213> ORGANISM: Artificial Sequence
<220> FEATURE:
<223> OTHER INFORMATION: Primer for mutant No. #12

<400> SEQUENCE: 125
gggtcattta cagcgaatga gaattttctg c                           31

<210> SEQ ID NO 126
<211> LENGTH: 31
<212> TYPE: DNA
<213> ORGANISM: Artificial Sequence
<220> FEATURE:
<223> OTHER INFORMATION: Primer for mutant No. #12

<400> SEQUENCE: 126
gcagaaaatt ctcattcgct gtaaatgacc c                           31

<210> SEQ ID NO 127
<211> LENGTH: 31
<212> TYPE: DNA
<213> ORGANISM: Artificial Sequence
<220> FEATURE:
<223> OTHER INFORMATION: Primer for mutant No. #13

<400> SEQUENCE: 127
gggtcattta cagcgcagga gaattttctg c                           31

<210> SEQ ID NO 128
<211> LENGTH: 31
<212> TYPE: DNA
<213> ORGANISM: Artificial Sequence
<220> FEATURE:
<223> OTHER INFORMATION: Primer for mutant No. #13

<400> SEQUENCE: 128
gcagaaaatt ctcctgcgct gtaaatgacc c                           31

<210> SEQ ID NO 129
<211> LENGTH: 31
<212> TYPE: DNA
<213> ORGANISM: Artificial Sequence
<220> FEATURE:
<223> OTHER INFORMATION: Primer for mutant No. #14

<400> SEQUENCE: 129
gggtcattta cagcgacaga gaattttctg c                           31

<210> SEQ ID NO 130
<211> LENGTH: 31
<212> TYPE: DNA
<213> ORGANISM: Artificial Sequence
<220> FEATURE:
<223> OTHER INFORMATION: Primer for mutant No. #14

<400> SEQUENCE: 130
gcagaaaatt ctctgtcgct gtaaatgacc c                           31

```
<210> SEQ ID NO 131
<211> LENGTH: 31
<212> TYPE: DNA
<213> ORGANISM: Artificial Sequence
<220> FEATURE:
<223> OTHER INFORMATION: Primer for mutant No. #15

<400> SEQUENCE: 131
gggtcattta cagcgtacga gaattttctg c                              31

<210> SEQ ID NO 132
<211> LENGTH: 31
<212> TYPE: DNA
<213> ORGANISM: Artificial Sequence
<220> FEATURE:
<223> OTHER INFORMATION: Primer for mutant No. #15

<400> SEQUENCE: 132
gcagaaaatt ctcgtacgct gtaaatgacc c                              31

<210> SEQ ID NO 133
<211> LENGTH: 31
<212> TYPE: DNA
<213> ORGANISM: Artificial Sequence
<220> FEATURE:
<223> OTHER INFORMATION: Primer for mutant No. #16

<400> SEQUENCE: 133
gggtcattta cagcgaagga gaattttctg c                              31

<210> SEQ ID NO 134
<211> LENGTH: 31
<212> TYPE: DNA
<213> ORGANISM: Artificial Sequence
<220> FEATURE:
<223> OTHER INFORMATION: Primer for mutant No. #16

<400> SEQUENCE: 134
gcagaaaatt ctccttcgct gtaaatgacc c                              31

<210> SEQ ID NO 135
<211> LENGTH: 31
<212> TYPE: DNA
<213> ORGANISM: Artificial Sequence
<220> FEATURE:
<223> OTHER INFORMATION: Primer for mutant No. #17

<400> SEQUENCE: 135
gggtcattta cagcgcgcga gaattttctg c                              31

<210> SEQ ID NO 136
<211> LENGTH: 31
<212> TYPE: DNA
<213> ORGANISM: Artificial Sequence
<220> FEATURE:
<223> OTHER INFORMATION: Primer for mutant No. #17

<400> SEQUENCE: 136
gcagaaaatt ctcgcgcgct gtaaatgacc c                              31

<210> SEQ ID NO 137
<211> LENGTH: 31
<212> TYPE: DNA
<213> ORGANISM: Artificial Sequence
<220> FEATURE:
<223> OTHER INFORMATION: Primer for mutant No. #18
```

```
<400> SEQUENCE: 137
gggtcattta cagcgcatga gaattttctg c                              31

<210> SEQ ID NO 138
<211> LENGTH: 31
<212> TYPE: DNA
<213> ORGANISM: Artificial Sequence
<220> FEATURE:
<223> OTHER INFORMATION: Primer for mutant No. #18

<400> SEQUENCE: 138
gcagaaaatt ctcatgcgct gtaaatgacc c                              31

<210> SEQ ID NO 139
<211> LENGTH: 31
<212> TYPE: DNA
<213> ORGANISM: Artificial Sequence
<220> FEATURE:
<223> OTHER INFORMATION: Primer for mutant No. #19

<400> SEQUENCE: 139
gggtcattta cagcggatga gaattttctg c                              31

<210> SEQ ID NO 140
<211> LENGTH: 31
<212> TYPE: DNA
<213> ORGANISM: Artificial Sequence
<220> FEATURE:
<223> OTHER INFORMATION: Primer for mutant No. #19

<400> SEQUENCE: 140
gcagaaaatt ctcatccgct gtaaatgacc c                              31

<210> SEQ ID NO 141
<211> LENGTH: 31
<212> TYPE: DNA
<213> ORGANISM: Artificial Sequence
<220> FEATURE:
<223> OTHER INFORMATION: Primer for mutant No. #20

<400> SEQUENCE: 141
gggtcattta cagcggaaga gaattttctg c                              31

<210> SEQ ID NO 142
<211> LENGTH: 31
<212> TYPE: DNA
<213> ORGANISM: Artificial Sequence
<220> FEATURE:
<223> OTHER INFORMATION: Primer for mutant No. #20

<400> SEQUENCE: 142
gcagaaaatt ctcttccgct gtaaatgacc c                              31

<210> SEQ ID NO 143
<211> LENGTH: 34
<212> TYPE: DNA
<213> ORGANISM: Artificial Sequence
<220> FEATURE:
<223> OTHER INFORMATION: Primer for mutant No. #21

<400> SEQUENCE: 143
gagaattttc tgccgggggtg cctgagctgt tcta                           34

<210> SEQ ID NO 144
<211> LENGTH: 34
```

```
<212> TYPE: DNA
<213> ORGANISM: Artificial Sequence
<220> FEATURE:
<223> OTHER INFORMATION: Primer for mutant No. #21

<400> SEQUENCE: 144
tagaacagct caggcacccc ggcagaaaat tctc                                34

<210> SEQ ID NO 145
<211> LENGTH: 34
<212> TYPE: DNA
<213> ORGANISM: Artificial Sequence
<220> FEATURE:
<223> OTHER INFORMATION: Primer for mutant No. #22

<400> SEQUENCE: 145
gagaattttc tgccggggtg cctgagctgt tcta                                34

<210> SEQ ID NO 146
<211> LENGTH: 34
<212> TYPE: DNA
<213> ORGANISM: Artificial Sequence
<220> FEATURE:
<223> OTHER INFORMATION: Primer for mutant No. #22

<400> SEQUENCE: 146
tagaacagct caggcacccc ggcagaaaat tctc                                34

<210> SEQ ID NO 147
<211> LENGTH: 34
<212> TYPE: DNA
<213> ORGANISM: Artificial Sequence
<220> FEATURE:
<223> OTHER INFORMATION: Primer for mutant No. #23

<400> SEQUENCE: 147
gattccgaat tttctgctgg cgtgcctgag ctgt                                34

<210> SEQ ID NO 148
<211> LENGTH: 34
<212> TYPE: DNA
<213> ORGANISM: Artificial Sequence
<220> FEATURE:
<223> OTHER INFORMATION: Primer for mutant No. #23

<400> SEQUENCE: 148
acagctcagg cacgccagca gaaaattcgg aatc                                34

<210> SEQ ID NO 149
<211> LENGTH: 34
<212> TYPE: DNA
<213> ORGANISM: Artificial Sequence
<220> FEATURE:
<223> OTHER INFORMATION: Primer for mutant No. #24

<400> SEQUENCE: 149
gattccgaat tttctgattg cgtgcctgag ctgt                                34

<210> SEQ ID NO 150
<211> LENGTH: 34
<212> TYPE: DNA
<213> ORGANISM: Artificial Sequence
<220> FEATURE:
<223> OTHER INFORMATION: Primer for mutant No. #24

<400> SEQUENCE: 150
```
acagctcagg cacgcaatca gaaaattcgg aatc					34

<210> SEQ ID NO 151
<211> LENGTH: 34
<212> TYPE: DNA
<213> ORGANISM: Artificial Sequence
<220> FEATURE:
<223> OTHER INFORMATION: Primer for mutant No. #25

<400> SEQUENCE: 151
gattccgaat tttctgtttg cgtgcctgag ctgt					34

<210> SEQ ID NO 152
<211> LENGTH: 34
<212> TYPE: DNA
<213> ORGANISM: Artificial Sequence
<220> FEATURE:
<223> OTHER INFORMATION: Primer for mutant No. #25

<400> SEQUENCE: 152
acagctcagg cacgcaaaca gaaaattcgg aatc					34

<210> SEQ ID NO 153
<211> LENGTH: 33
<212> TYPE: DNA
<213> ORGANISM: Artificial Sequence
<220> FEATURE:
<223> OTHER INFORMATION: Primer for mutant No. #26

<400> SEQUENCE: 153
tccgaatttt ctgccggggt gcctgagctg ttc					33

<210> SEQ ID NO 154
<211> LENGTH: 33
<212> TYPE: DNA
<213> ORGANISM: Artificial Sequence
<220> FEATURE:
<223> OTHER INFORMATION: Primer for mutant No. #26

<400> SEQUENCE: 154
gaacagctca ggcaccccgg cagaaaattc gga					33

<210> SEQ ID NO 155
<211> LENGTH: 43
<212> TYPE: DNA
<213> ORGANISM: Artificial Sequence
<220> FEATURE:
<223> OTHER INFORMATION: Primer for mutant No. #27

<400> SEQUENCE: 155
agcgattccg aattttctgc tggggtgcct gagctgttct aag					43

<210> SEQ ID NO 156
<211> LENGTH: 43
<212> TYPE: DNA
<213> ORGANISM: Artificial Sequence
<220> FEATURE:
<223> OTHER INFORMATION: Primer for mutant No. #27

<400> SEQUENCE: 156
cttagaacag ctcaggcacc ccagcagaaa attcggaatc gct					43

<210> SEQ ID NO 157
<211> LENGTH: 43
<212> TYPE: DNA
<213> ORGANISM: Artificial Sequence

```
<220> FEATURE:
<223> OTHER INFORMATION: Primer for mutant No. #28

<400> SEQUENCE: 157
agcgattccg aattttctga ttgggtgcct gagctgttct aag          43

<210> SEQ ID NO 158
<211> LENGTH: 43
<212> TYPE: DNA
<213> ORGANISM: Artificial Sequence
<220> FEATURE:
<223> OTHER INFORMATION: Primer for mutant No. #28

<400> SEQUENCE: 158
cttagaacag ctcaggcacc caatcagaaa attcggaatc gct          43

<210> SEQ ID NO 159
<211> LENGTH: 43
<212> TYPE: DNA
<213> ORGANISM: Artificial Sequence
<220> FEATURE:
<223> OTHER INFORMATION: Primer for mutant No. #29

<400> SEQUENCE: 159
agcgattccg aattttctgt ttgggtgcct gagctgttct aag          43

<210> SEQ ID NO 160
<211> LENGTH: 43
<212> TYPE: DNA
<213> ORGANISM: Artificial Sequence
<220> FEATURE:
<223> OTHER INFORMATION: Primer for mutant No. #29

<400> SEQUENCE: 160
cttagaacag ctcaggcacc caaacagaaa attcggaatc gct          43

<210> SEQ ID NO 161
<211> LENGTH: 23
<212> TYPE: DNA
<213> ORGANISM: Artificial Sequence
<220> FEATURE:
<223> OTHER INFORMATION: Forward Primer

<400> SEQUENCE: 161
acatatggat agcgtgtgcc cgc                                23

<210> SEQ ID NO 162
<211> LENGTH: 27
<212> TYPE: DNA
<213> ORGANISM: Artificial Sequence
<220> FEATURE:
<223> OTHER INFORMATION: Backward Primer

<400> SEQUENCE: 162
taagcttatt aattaaaaca ctggaac                            27

<210> SEQ ID NO 163
<211> LENGTH: 23
<212> TYPE: DNA
<213> ORGANISM: Artificial Sequence
<220> FEATURE:
<223> OTHER INFORMATION: Forward Primer

<400> SEQUENCE: 163
acatatggat agcgtgtgcc cgc                                23
```

```
<210> SEQ ID NO 164
<211> LENGTH: 29
<212> TYPE: DNA
<213> ORGANISM: Artificial Sequence
<220> FEATURE:
<223> OTHER INFORMATION: Backward Primer

<400> SEQUENCE: 164
cggatcctta acaaactgta ttctgcttc                                  29

<210> SEQ ID NO 165
<211> LENGTH: 23
<212> TYPE: DNA
<213> ORGANISM: Artificial Sequence
<220> FEATURE:
<223> OTHER INFORMATION: Forward Primer

<400> SEQUENCE: 165
acatatggat agcgtgtgcc cgc                                        23

<210> SEQ ID NO 166
<211> LENGTH: 28
<212> TYPE: DNA
<213> ORGANISM: Artificial Sequence
<220> FEATURE:
<223> OTHER INFORMATION: Backward Primer

<400> SEQUENCE: 166
cggatcctta tgtggtgcct gagtcctc                                   28
```

MODIFIED HUMAN TUMOR NECROSIS FACTOR RECEPTOR-I POLYPEPTIDE OR FRAGMENT THEREOF, AND METHOD FOR PREPARING SAME

CROSS-REFERENCE TO RELATED APPLICATIONS

This application is a U.S. national phase under the provisions of 35 U.S.C. §371 of International Patent Application No. PCT/KR11/06621 filed Sep. 7, 2011, which in turn claims priority of Korean Patent Application No. 10-2010-0089395 filed Sep. 13, 2010. The disclosures of such international patent application and Korean priority patent application are hereby incorporated herein by reference in their respective entireties, for all purposes.

TECHNICAL FIELD

The present invention relates to a modified human tumor necrosis factor receptor-I polypeptide or a fragment thereof which has improved binding affinity to a tumor necrosis factor in vivo or ex vivo and a method for producing the same.

BACKGROUND ART

Inflammation is the body's defense response which is induced by antigenic stimulation. An inflammatory response may worsen pathologically when inflammation takes place even after the removal of injurious antigenic substances or an inflammatory response is induced by an inappropriate stimulus such as an auto-antigen. Such an inflammatory response involves a variety of cytokines. In particular, as a cytokine which serves to control inflammation, a tumor necrosis factor (hereinafter, referred to as "TNF") was identified.

TNF was originally discovered as a protein which eliminates tumor cells (Carswell et al., PNAS 72:3666-3670, 1975; Old et al., Science 230: 630-632, 1985; and Beutler et al., Nature 316:552-554, 1985). TNF is a class of cytokines produced by numerous cell types, including monocytes and macrophages, and is directly involved in inflammatory responses. At least two TNFs (TNF-α and TNF-β) have been previously described, and each is active as a trimeric molecule and is believed to initiate intracellular signaling by crosslinking receptors (Engelmann et al., J. Biol. Chem., 265:14497-14504). TNFs induce inflammatory responses in vivo to regulate cell-mediated immune responses and defense mechanisms and have important physiological effects on a number of different target cells (Selby et al., Lancep 1:483, 1988; Starnes et al., J. Clin. Invest 82:1321, 1988; Oliff et al., Cell 50; 555, 1987; Waage et al., Lancept 1:355, 1987; and Aggarwal et al., Nat. Rev. Immunol. 3:745-756, 2003). However, it was demonstrated that an excess of TNFs results in a pathological condition such as rheumatoid arthritis, degenerative arthritis, psoriasis or Crohn's disease, and suppression of TNFs exhibits therapeutic effects on the diseases (Feldmann et al., Nat. Med. 9:1245-1250, 2003; Kooloos et al., Drug Discov. Today 12:125-131, 2007; Rutgeerts et al., Gastroenterology 126:1593-1610, 2004; Rothe et al., Nature 364:798-802, 1993; Kafrouni et al., J. Leukocyte Biol. 74:564-571, 2003; Rahman et al., Plos Pathog. 2:e4, 2006; Chan et al., J. Biol. Chem. 278:51613-61621, 2003; and Wajant et al., Cell Death Differ. 10:45-65, 2003).

Tumor necrosis factor receptor (hereinafter, referred to as "TNFR") is a cytokine receptor which binds to TNF.

Two types of TNFRs, known as p55-TNFRI and p75-TNFRII, have been currently discovered. Expression of TNFRI can be demonstrated in almost every mammalian cell while TNFRII expression is largely limited to cells of the immune system and endothelial cells.

The two TNF receptors exhibit 28% amino acid sequence similarity therebetween. Both receptors have an extracellular domain and have four cysteine-rich domains.

The cytoplasmic portion of TNFRI contains a "death domain" which initiates apoptotic signaling. TNFRII has no death domain and the function thereof has not been yet clearly defined. In addition, TNFRI and TNFRII exhibit a difference in terms of affinity for TNF-α which is a ligand. It is known that TNFRI exhibits an affinity 30 times or higher than that of TNFRII (Tartaglia et al., J. Biol. Chem. 268:18542-18548, 1993; and Bernard et al., Cytokine 7:759-770, 1995). Due to such affinity difference, a variety of attempts have been made for the development of pharmaceuticals regarding TNFRI.

TNFR adhering to the cell surface is cleaved by protease to produce soluble TNFR. The soluble TNFR neutralizes an excess of TNF to control the level of TNF. In cases such as autoimmune disease and chronic inflammation excessively high levels of TNF overwhelms the ability to self-regulate.

In order to artificially control TNF signaling, various strategies of blocking TNF have been attempted including inhibition of TNF synthesis, inhibition of TNF secretion or shedding, and inhibition of TNF signaling. Among TNF blocking methods, a method of blocking TNF signaling by preventing binding of TNFR to TNF has been applied for the development of pharmaceuticals. For example, etanercept, which is prepared by fusing a TNFRII extracellular region to the Fc region of an antibody, and antibodies capable of binding to TNF, adalimumab and infliximab have been used globally as a therapeutic agent for treating rheumatoid arthritis, psoriasis, ankylosing spondylitis, or the like.

Lenercept, which is a fusion protein of an antibody Fc to a TNFRI extracellular domain produced by applying the same technique as in the anti-rheumatoid arthritis drug etanercept, has completed a phase II clinical trial in Europe and USA (Furst et al., J. Rheumatol. 30:2123-2126, 2003; and Rau et al., J. Rheumatol. 30:680-690, 2003 Arbraham et al., Crit. Care Med. 29:503-510, 2001). In addition, research has been carried out for a TNFRI dimer and a pegylated soluble TNFRI molecule (Carl et al., Ann. Rheum. Dis. 58:173-181, 1999; Solorzano et al., J. Appl. Physiol. 84:1119-1130, 1998; Carl et al., Advanced Drug Delivery Reviews 55:1315-1336, 2003; Honghui et al., J. Clin. Pharmacol. 45:490-497, 2005; and Yugal et al., The American Journal of Pathology 172: 1411-1418, 2008).

Further, as an approach to reduce immunogenicity of TNFRI and increase the ability of TNFRI to bind with TNF, modification of amino acid sequences has been studied. In particular, a TNFRI mutant, against which the occurrence of an antibody has been decreased through partial substitution of the amino acid sequence of TNFRI, and a TNFRI mutant, which has an increased ability of TNFRI to bind with TNF, are known (U.S. Pat. No. 7,144,987).

Research has been actively made to find an active site responsible for binding of TNFR to TNF, and it is known that the fourth domain of TNFR is not essential for binding with TNF, and when deletion of the second and third domains results in loss of TNF binding activity (Corcoran et al., Eur. J. Biochem. 233:831-840, 1994; Chin-Hsueh et al., J. Biol. Chem. 270:2874-2878, 1995; and Scallon et al., Cytokine 7:759-770, 1995). Further, a certain region of the third domain for binding of TNFRI to TNF may be made deficient, and the amino acid sequence consisting of amino acid residues 59 to 143 of a human TNFRI polypeptide (SEQ ID NO:

1) is known to be a region showing a biological activity of TNFRI (U.S. Pat. No. 6,989,147).

Therefore, since binding of TNFRI to TNF is made in this region, other regions may include considerable added groups, eliminated groups or substituted groups. In addition, no sugar chain is linked to the region.

Meanwhile, natural (wild type) TNFRI regulates the function of TNF in the cell by binding to the TNFα, but natural TNFRI does not have high affinity to the TNFα comparing to an antibody. As a consequence of relatively low affinity of TNFRI to the TNFα, inhibitory effect of TNFα by TNFRI is weaker than the one by the antibody.

Therefore, it is necessary to screen TNFRI which has strong affinity to the TNFα to develop protein therapeutics based on the TNFRI.

DISCLOSURE OF THE INVENTION

Technical Problem

Therefore, the present invention is intended to provide a modified human tumor necrosis factor receptor-I (TNFRI) polypeptide or a fragment thereof, which has improved binding affinity to a tumor necrosis factor in vivo or ex vivo and a method for producing the same.

Technical Solution

Unless stated otherwise, all technical and scientific terms used in the specification, examples and appended claims have the meanings defined below.

As used herein, the term "human tumor necrosis factor receptor-I" or "human tumor necrosis factor receptor-I polypeptide" (hereinafter, referred to as "TNFRI" or "TNFRI polypeptide") refers to a polypeptide consisting of 455 amino acids derived from a human and capable of binding to TNF.

As used herein, the term "human tumor necrosis factor receptor-I fragment" or "human tumor necrosis factor receptor-I polypeptide fragment" (hereinafter, referred to as "TNFRI fragment" or "TNFRI polypeptide fragment") refers to a fragment of TNFRI which has an amino acid sequence 100% identical to a corresponding amino acid sequence of TNFRI and which has a deletion of at least one amino acid residue in the TNFRI. The deleted amino acid residue(s) may be located at any position of the polypeptide, such as the N-terminus, the C-terminus, or in between these. The fragment shares at least one biological property with full-length TNFRI. Representative is a fragment consisting of a 105, 126, and 171 amino acid sequence extending from 41$^{st}$ amino acid residue of the N-terminus of TNFRI, each being designated as TNFRI105, TNFRI126 and TNFRI171, respectively, in the present invention.

As used herein, the term "TNFRI variant" or "TNFRI mutant" or "TNFRI fragment variant", "TNFRI fragment mutant" or "modified TNFRI polypeptide", or "modified TNFRI polypeptide fragment" refers to a TNFRI polypeptide or a fragment thereof which shares a sequence identity of less than 100% with the TNFRI polypeptide or a fragment thereof isolated from the native or recombinant cells as defined below. Typically, the TNFRI variant has an amino acid sequence identity of approximately 70% or higher with a wild-type or natural TNFRI or TNFRI fragment. The sequence identity is preferably at least approximately 75%, more preferably at least approximately 80%, still more preferably at least approximately 85%, even more preferably at least approximately 90%, and most preferably at least approximately 95%.

As used herein, the term "triple variant" refers to a variant with a mutation at three positions in the amino acid sequence of a human tumor necrosis factor receptor-I or human tumor necrosis factor receptor-I fragment.

As used herein, the term "quadruple variant" refers to a variant with a mutation at four positions in the amino acid sequence of a human tumor necrosis factor receptor-I or human tumor necrosis factor receptor-I fragment.

As used herein, the term "quintuple variant" refers to a variant with a mutation at five positions in the amino acid sequence of a human tumor necrosis factor receptor-I or human tumor necrosis factor receptor-I fragment.

As used herein, the term "TNFRIm" refers to a TNFRI fragment having an amino acid sequence composed of m amino acid residues extending from the 41st amino acid residue from the N-terminus in an amino acid sequence of TNFRI. For example, the TNFRI105 fragment refers to a TNFRI fragment having a 105-amino acid sequence extending from the 41st amino acid residue from the TNFRI N-terminus. An another example, the TNFRI126 fragment refers to a TNFRI fragment having a 126-amino acid sequence extending from the 41st amino acid residue from the TNFRI N-terminus.

As used herein, the term "Met-TNFRIm" refers to a TNFRI fragment having an amino acid sequence consisting of an m amino acid residues extending from the 41$^{st}$ amino acid residue of the TNFRI N-terminus in which methionine originally absent in TNFRI amino acid sequence has been added to the N-terminus for the purpose of expression of TNFRI in $E.\ coli$.

As used herein, the symbol "xAz" refers to the substitution of amino acid residue, x with z at position A from the N-terminus (based on the amino acid sequence of TNFRI) in an amino acid sequence of TNFRI or TNFRI fragment. For example, K48Q refers to the substitution of amino acid residue, lysine (Lys) with glutamine (Gln) at position 48 from the N-terminus in the amino acid sequence of TNFRI.

The present invention relates to a modified TNFRI polypeptide or a fragment thereof which has improved binding affinity to a tumor necrosis factor in vivo or ex vivo, a method for producing the same, and use thereof.

As a result of extensive and intensive studies to develop a TNFRI variant having improved binding affinity to the TNF, the inventors of the present application have confirmed that TNFRI variants having modification of more than 4 amino acid residues in the site of natural TNFRI which are anticipated to be involved in binding to TNF has improved biding affinity to the TNF comparing to natural TNFRI without modification in the site.

Therefore, the present invention provides a modified TNFRI polypeptide or a fragment thereof having improved binding affinity to the TNF through the amino acid modifications (substitution) at more than 4 specific positions of an amino acid sequence of a natural TNFRI polypeptide or a fragment thereof.

The modified TNFRI polypeptide or a fragment thereof in accordance with the present invention effectively inhibits the TNF activity by stably binding to the TNF, and it can be easily produced in microbial cells as well as animal cell because it does not have any sugar chain.

More specifically, the present invention will be reviewed hereinafter.

The present invention provides a modified TNFRI polypeptide or a fragment thereof having improved binding affinity to the TNF, and the modified TNFRI polypeptide or the fragment thereof comprises amino acid modifications at least at the position of 92, 95, 97 and 98 in the amino acid sequence of a natural human TNFRI polypeptide as set forth in SEQ ID NO: 1 or a fragment thereof. In addition, the modified TNFRI polypeptide or the fragment thereof the present invention comprises additional amino acid modifications at the position of 93 as well as modification at the position of 92, 95, 97 and 98 in the amino acid sequence of a natural human TNFRI polypeptide as set forth in SEQ ID NO: 1 or a fragment thereof.

Amino acid modifications at the above-specified positions are modifications to improve binding affinity to TNF as compared to an unmodified TNFRI polypeptide or a fragment thereof, representative is substitution of amino acid. However, as long as improved binding affinity is retained, additional chemical modifications of amino acids at the above-specified positions, such as post-translational modifications of a protein, for example, glycosylation by a carbohydrate moiety, acylation (e.g., acetylation or succinylation), methylation, phosphorylation, hesylation, carbamylation, sulfation, prenylation, oxidation, guanidination, amidination, carbamylation (e.g., carbamoylation), trinitrophenylation, nitration, and PEGylation are also can be included.

The present invention provides a modified TNFRI polypeptide or a fragment thereof comprising:
substitution of S with I, L, F, M, W, Q, T, Y, K, H, E, A, V, P, N or R, preferably I, L, F, M, W, Q, T, Y, K, H or E, more preferably I, F, M, W, Y, K or H at position 92;
substitution of H with F at position 95;
substitution of R with P, L or I, preferably P at position 97; and
substitution of H with A or G at position 98;
in the amino acid sequence of a natural human TNFRI polypeptide as set forth in SEQ ID NO: 1 or a fragment thereof.

Preferably, the present invention provides a modified TNFRI polypeptide or a fragment thereof comprising:
substitution of S with I, L, F, M, W, Q, T, Y, K, H, E, A, V, P, N or R, preferably I, L, F, M, W, Q, T, Y, K, H or E, more preferably I, F, M, W, Y, K or H at position 92;
substitution of E with P at position 93;
substitution of H with F at position 95;
substitution of R with P, L or I, preferably P at position 97; and
substitution of H with A or G at position 98;
in the amino acid sequence of a natural human TNFRI polypeptide as set forth in SEQ ID NO: 1 or a fragment thereof.

Further, the present invention provides a modified TNFRI polypeptide or a fragment thereof comprising modifications selected from the group of
S92I/H95F/R97P/H98A, S92F/H95F/R97P/H98A, S92M/H95F/R97P/H98A, S92W/H95F/R97P/H98A, S92Y/H95F/R97P/H98A, S92K/H95F/R97P/H98A, S92H/H95F/R97P/H98A, S92I/H95F/R97P/H98G, and S92M/H95F/R97P/H98G in the amino acid sequence of a natural human TNFRI polypeptide as set forth in SEQ ID NO: 1 or a fragment thereof.

Preferably, the present invention provides a modified TNFRI polypeptide or a fragment thereof comprising modifications selected from the group of
S92I/H95F/R97P/H98A, S92M/H95F/R97P/H98A, S92I/H95F/R97P/H98G, and S92M/H95F/R97P/H98G in the amino acid sequence of a natural human TNFRI polypeptide as set forth in SEQ ID NO: 1 or a fragment thereof.

The term TNFRI fragment of a native TNFRI refers to a portion of a natural TNFRI, which exhibits a substantially equivalent effect to a natural TNFRI. Particularly, in the present invention, an amino acid sequence composed of amino acid residues 41 to 145 (SEQ ID NO: 2; TNFRI105) of the amino acid sequence of the natural TNFRI as set forth in SEQ ID NO: 1; an amino acid sequence composed of amino acid residues 41 to 166 (SEQ ID NO: 3; TNFRI126) of the amino acid sequence of the natural TNFRI as set forth in SEQ ID NO: 1; and an amino acid sequence composed of amino acid residues 41 to 211 (SEQ ID NO: 4; TNFRI171) of the amino acid sequence of the natural TNFRI as set forth in SEQ ID NO: 1.

The term "fragment" of a modified TNFRI polypeptide refers to a portion of a modified TNFRI polypeptide which exhibits an effect substantially equivalent to that of the modified TNFRI polypeptide and can be easily produced by those skilled in the art.

Therefore, the modified TNFRI polypeptide or a fragment thereof having improved binding affinity to the TNF in accordance with the present invention encompasses those illustrated below.

The present invention provides a modified TNFRI polypeptide or a fragment thereof comprising:
substitution of S with I, L, F, M, W, Q, T, Y, K, H, E, A, V, P, N or R, preferably I, L, F, M, W, Q, T, Y, K, H or E, more preferably I, F, M, W, Y, K or H at position 92;
substitution of H with F at position 95;
substitution of R with P, L or I, preferably P at position 97; and
substitution of H with A or G at position 98;
in an amino acid sequence composed of amino acid residues 41 to 145 of the amino acid sequence of the natural TNFRI set forth in SEQ ID NO: 1 (TNFRI105).

Preferably, the present invention provides a modified TNFRI polypeptide or a fragment thereof comprising modifications selected from the group of S92I/H95F/R97P/H98A, S92F/H95F/R97P/H98A, S92M/H95F/R97P/H98A, S92W/H95F/R97P/H98A, S92Y/H95F/R97P/H98A, S92K/H95F/R97P/H98A, S92H/H95F/R97P/H98A, S92I/H95F/R97P/H98G, and S92M/H95F/R97P/H98G, more preferably, selected from the group of S92I/H95F/R97P/H98A, S92M/H95F/R97P/H98A, S92I/H95F/R97P/H98G, and S92M/H95F/R97P/H98G in an amino acid sequence composed of amino acid residues 41 to 145 of the amino acid sequence of the natural TNFRI set forth in SEQ ID NO: 1 (TNFRI105).

The present invention provides a modified TNFRI polypeptide or a fragment thereof comprising:
substitution of S with I, L, F, M, W, Q, T, Y, K, H, E, A, V, P, N or R, preferably I, L, F, M, W, Q, T, Y, K, H or E, more preferably I, F, M, W, Y, K or H at position 92;
substitution of H with F at position 95;
substitution of R with P, L or I, preferably P at position 97; and
substitution of H with A or G at position 98;
in an amino acid sequence composed of amino acid residues 41 to 166 of the amino acid sequence of the natural TNFRI set forth in SEQ ID NO: 1 (TNFRI126).

Preferably, the present invention provides a modified TNFRI polypeptide or a fragment thereof comprising modifications selected from the group of S92I/H95F/R97P/H98A, S92F/H95F/R97P/H98A, S92M/H95F/R97P/H98A, S92W/H95F/R97P/H98A, S92Y/H95F/R97P/H98A, S92K/H95F/R97P/H98A, S92H/H95F/R97P/H98A, S92I/H95F/R97P/H98G, and S92M/H95F/R97P/H98G, more preferably, selected from the group of S92I/H95F/R97P/H98A, S92M/H95F/R97P/H98A, S92I/H95F/R97P/H98G, and S92M/H95F/R97P/H98G in an amino acid sequence composed of amino acid residues 41 to 166 of the amino acid sequence of the natural TNFRI set forth in SEQ ID NO: 1 (TNFRI126).

The present invention provides a modified TNFRI polypeptide or a fragment thereof comprising:

substitution of S with I, L, F, M, W, Q, T, Y, K, H, E, A, V, P, N or R, preferably I, L, F, M, W, Q, T, Y, K, H or E, more preferably I, F, M, W, Y, K or H at position 92;

substitution of H with F at position 95;

substitution of R with P, L or I, preferably P at position 97; and substitution of H with A or G at position 98;

in an amino acid sequence composed of amino acid residues 41 to 211 of the amino acid sequence of the natural TNFRI set forth in SEQ ID NO: 1 (TNFRI171).

Preferably, the present invention provides a modified TNFRI polypeptide or a fragment thereof comprising modifications selected from the group of S92I/H95F/R97P/H98A, S92F/H95F/R97P/H98A, S92M/H95F/R97P/H98A, S92W/H95F/R97P/H98A, S92Y/H95F/R97P/H98A, S92K/H95F/R97P/H98A, S92H/H95F/R97P/H98A, S92I/H95F/R97P/H98G, and S92M/H95F/R97P/H98G, more preferably, selected from the group of S92I/H95F/R97P/H98A, S92M/H95F/R97P/H98A, S92I/H95F/R97P/H98G, and S92M/H95F/R97P/H98G in an amino acid sequence composed of amino acid residues 41 to 211 of the amino acid sequence of the natural TNFRI set forth in SEQ ID NO: 1 (TNFRI171).

The present invention provides a modified TNFRI polypeptide or a fragment thereof containing modifications corresponding to the position of 92, 95, 97 and 98 in the amino acid sequence as set forth in SEQ ID NO: 1, and having sequence homology of more than 90%, more than 95%, more than 96%, more than 97%, more than 98% or more than 99% with the amino acid sequence as set forth in SEQ ID NO: 1.

More specifically, the present invention provides a modified TNFRI polypeptide or a fragment thereof comprising:

substitution of S with I, L, F, M, W, Q, T, Y, K, H, E, A, V, P, N or R, preferably I, L, F, M, W, Q, T, Y, K, H or E, more preferably I, F, M, W, Y, K or H at the corresponding to the position 92;

substitution of H with F at the corresponding to the position 95;

substitution of R with P, L or I, preferably P at the corresponding to the position 97; and substitution of H with A or G at the corresponding to the position 98;

in an amino acid sequence of the natural TNFRI set forth in SEQ ID NO: 1.

The above modified TNFRI polypeptide or a fragment thereof can also comprise substitution of E with P at the corresponding to the position 93 in an amino acid sequence of the natural TNFRI set forth in SEQ ID NO: 1.

Further, the present invention provides a modified TNFRI polypeptide or a fragment thereof containing the above-specified amino acid modifications or the corresponding modifications in the polypeptide substantially identical to a TNFRI polypeptide having the amino acid sequence as set forth in SEQ ID NO: 1. The term "polypeptide substantially identical to a TNFRI polypeptide having the amino acid sequence as set forth in SEQ ID NO: 1" refers to a polypeptide containing numbers and kinds of amino acid modifications not detrimental to an intrinsic activity of TNFRI, that is, amino acid substitution, deletion, addition or other modifications.

The above-mentioned variant has sequence homology of more than 90%, more than 95%, more than 96%, more than 97%, more than 98%, or more than 99% with a polypeptide having the sequence as set forth in SEQ ID NO: 1, except the amino acid modifications of the present invention for improving binding affinity to TNF, and includes allelic variant isoforms of human TNFRI polypeptide, tissue-specific isoforms and allelic variants thereof, synthetic variants with one or more amino acid mutations, replacements, deletions, insertions or additions, synthetic molecules prepared by translation of nucleic acids, proteins isolated from human and non-human tissue and cells, chimeric TNFRI polypeptides and modified forms thereof.

As used herein, the term "corresponding to the position" refers to a position of a residue identified to be functionally unchangeable upon sequence alignment with the amino acid sequence of a natural human TNFRI polypeptide as set forth in SEQ ID NO: 1. Those skilled in the art can readily identify modifications of residues that correspond between or among such polypeptides. For example, by aligning the sequences of TNFRI polypeptides, one of skill in the art can identify corresponding residues, using conserved and identical amino acid residues as guides.

The present invention provides a modified TNFRI polypeptide or a fragment thereof comprising amino acid sequences selected from SEQ ID NO:10, 12-18, 20-26, 28-35, 37, 38, 40, 41-48, 50-56, 58-65, 67, 68, 70, 72-78, 80-86, 88-95, 97, and 98, preferably, selected from SEQ ID NO: 10, 16-18, 23, 24, 26, 29, 30, 40, 46-48, 53, 54, 56, 59, 60, 70, 76-78, 83, 84, 86, 89, and 90, more preferably, selected from 10, 17, 29, 30, 40, 47, 59, 60, 70, 77, 89 and 90.

The modified TNFRI polypeptide or a fragment thereof in accordance with the present invention may further contain other chemical modifications such as post-translational modifications of a protein, for example, glycosylation by a carbohydrate moiety, acylation (e.g., acetylation or succinylation), methylation, phosphorylation, hesylation, carbamylation, sulfation, prenylation, oxidation, guanidination, amidination, carbamylation (e.g., carbamoylation), trinitrophenylation, nitration, and PEGylation, for the purpose of increasing protease resistance, decreasing immunogenicity, or maintaining or enhancing biological activity, in addition to the above-mentioned amino acid modifications.

Also, a polymeric polypeptide (or referred to as "polypeptide complex") including at least two of the foregoing modified TNFRIs or modified TNFRI fragments is included within the range of the modified TNFRI or modified TNFRI fragment of the present invention.

Further, the present invention provides a gene encoding the foregoing TNFRI polypeptide or a fragment thereof.

The gene encoding a TNFRI polypeptide or a fragment thereof in accordance with the present invention includes a gene engineered for optimization of the expression in *E. coli*. Due to the difference in gene codon between human and *E. coli*, when a human gene is expressed in *E. coli*, an expression yield of the gene is low. For this reason, a gene engineered to be suitable for the expression in *E. coli* based on a human TNFRI gene, for example the TNFRI gene of SEQ ID NO: 5 may be used in the present invention. Such a gene exhibits a higher expression level than a human TNFRI gene, when it is inserted into an *E. coli* expression vector (for example, pET44a (Cat. No: 71122-3, Novagen)) and then expressed in an *E. coli* cell with no addition of codon (e.g.: BL21(DE3)). Therefore, using the above gene, a TNFRI fragment and a TNFRI variant may be efficiently produced in *E. coli*.

Further, the present invention provides a vector containing the same gene. The vector that can be used for the introduction of a gene in the present invention may be a vector known in the art, preferably a vector having a cleavage map of FIG. 1.

Further, the present invention provides transformed cell (microbial or animal cell) with the vector. The microbial or animal cell that can be used for the transformation of a vector in the present invention may be a known microbial or animal cell for transformation used in the art, preferably an *E. coli* cell, a CHO cell, or an HEK293 cell, and more preferably an *E. coli* cell (for example, *E. coli* BL21(DE3)).

The present invention provides a method for producing TNFRI using *E. coli*.

TNFRI may be also produced by using an animal cell (Bernie et al., The Journal of Pharmacology and Experimental Therapeutics. 301: 418-426, 2002; and Scallon et al., Cytokine. 7:759-770, 1995).

Since when it is expressed in *E. coli*, TNFRI is expressed in the form of an inclusion body which is not conformationally active, a process of refolding into an active protein is required (Silvia et al., Analytical Biochemistry 230: 85-90, 1995; and Karin et al., Cytokine. 7:26-38, 1995). Therefore, the modified TNFRI polypeptide or a fragment thereof in accordance with the present invention may be produced by expressing TNFRI in the form of an inclusion body in *E. coli*, refolding the expressed TNFRI into active TNFRI, and purifying the active TNFRI by using gel filtration chromatography or the like. Alternatively, the modified TNFRI polypeptide or a fragment thereof in accordance with the present invention may be produced in the form of a soluble protein instead of an inclusion body granules in *E. coli*, using an expression method involving attachment of a hydrophilic fusion protein, a low-temperature culture method, or the like. In Examples of the present invention, TNFRI as a soluble protein is produced in *E. coli* by linking a hydrophilic NusA protein to the N-terminus of a TNFRI protein.

Further, the present invention provides a method for producing a TNFRI polypeptide or a fragment thereof, including introducing the gene into a suitable vector, transforming the vector into a host cell to give a transformant, and culturing the transformant in a medium to express the TNFRI polypeptide or a fragment thereof.

Further, the present invention provides a method for the treatment of a TNF-mediated disease or internal symptom (hereinafter, referred to as "TNF-mediated disease"). Examples of the TNF-mediated disease, the related sequelae and symptoms associated therewith include: adult respiratory distress syndrome; anorexia; cancer (e.g., leukemia); chronic fatigue syndrome; graft-versus-host rejection; hyperalgesia; inflammatory bowel disease; neuroinflammatory disease; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia rheumatica and giant cell arteritis); septic shock; radiotherapy-induced side effects; systemic lupus erythematous; temporomandibular joint disease; thyroiditis and tissue transplantation.

Further, the present invention provides a composition for the prevention or treatment of rheumatoid arthritis or TNF-mediated disease, containing the modified TNFRI polypeptide or a fragment thereof.

Further, the present invention provides a composition for the prevention or treatment of rheumatoid arthritis or TNF-mediated disease, containing a gene encoding the modified TNFRI polypeptide or a fragment thereof, a vector containing the gene or a microbial or animal cell transformed with the vector.

Further, the present invention provides a method for treating adult respiratory distress syndrome; anorexia; cancer (e.g., leukemia); chronic fatigue syndrome; graft-versus-host rejection; hyperalgesia; inflammatory bowel disease; neuroinflammatory disease; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjogren's syndrome, rheumatic fever, polychondritis and polymyalgia rheumatica and giant cell arteritis); septic shock; radiotherapy-induced side effects; systemic lupus erythematous; temporomandibular joint disease; thyroiditis or tissue transplantation, including administering the (pharmaceutical) composition to the patients.

The pharmaceutical composition of the present invention may be administered via oral, sublingual, rectal, dermal, subcutaneous, intramuscular, intraperitoneal, intravenous or intraarterial.

The pharmaceutical composition may be prepared for storage or administration by mixing a TNFRI variant with pharmaceutically acceptable carriers, excipients or stabilizers. Acceptable carriers, excipients or stabilizers are nontoxic to recipients in the dosages and concentrations employed, and include buffers such as phosphate, citrate, acetate and other organic acid salts; antioxidants such as ascorbic acid; low-molecular weight (less than about 10 residues in length) peptides including polyarginine and proteins such as serum albumin, gelatin or immunoglobulin; hydrophilic polymers such as polyvinylpyrrolidone; amino acids such as glycine, glutamic acid, aspartic acid or arginine; and other carbohydrates including monosaccharides, disaccharides, cellulose and derivatives thereof, glucose, mannose or dextrins; chelating agents such as EDTA; sugar alcohols such as mannitol or sorbitol; counterions such as sodium; and/or non-ionic surfactants such as Tween, Pluronics or polyethylene glycol (PEG).

The pharmaceutical composition of the present invention may be formulated in the form of a sterile composition for injection according to a conventional method known in the art. The sterile composition for injection may contain a solution or suspension of the active compound in a vehicle such as water or naturally occurring vegetable oil like sesame, peanut or cottonseed oil or a synthetic fatty vehicle like ethyl oleate. The sterile composition for injection may be incorporated into a buffer, a preservative, an antioxidant and the like according to an accepted pharmaceutical practice.

A modified TNFRI polypeptide or a fragment thereof, or a gene encoding the same, or a vector containing the same gene, or a microbial or animal cell transformed with the vector in accordance with the present invention is incorporated in a therapeutically effective amount for the TNF-mediated disease in a pharmaceutical composition.

As used herein, the term "therapeutically effective amount" refers to the amount/dose of an active ingredient or pharmaceutical composition that is sufficient to elicit an effective response (i.e., a biological or medical response of an animal or human sought by a researcher, veterinarian, medical doctor or other clinician) upon administration to a subject. The therapeutically effective amount is intended to encompass an amount to produce symptomatic alleviation of the disease or disorder being treated. It is apparent to those skilled in the art that the therapeutically effective amount and dosing frequency of the active ingredient of the present invention will vary depending on desired effects. Therefore, an optimum dosage can be readily determined by those skilled in the art and may be adjusted according to various factors such as type and severity of the disease, contents of active ingredients and other ingredients in the composition, dosage form, and the age, weight, physical condition and gender of the subject, as well as diet, administration timing and route and excretion rate of the composition, duration of treatment, and concurrent medication. For example, for adults, the TNFRI variant of the present invention is preferably administered at a dose of 0.01 to 1,000 mg/weight-kg once a day, and more preferably 0.1 to 100 mg/weight-kg once a day.

The modified TNFRI polypeptide or a fragment thereof in accordance with the present invention may be administered as an addition for other therapies and may be administered with other pharmaceutical compositions suitable for the indication being treated. The TNFRI polypeptide or a fragment thereof in accordance with the present invention and any of one or more known or novel anti-inflammatory drugs may be administered separately or in combination. Information regarding the compounds corresponding to such drugs can be found in "The Merck Manual of Diagnosis and Therapy", Sixteenth Edition, Merck, Sharp & Dohme Research Laboratories, Merck & Co., Rahway, N.J. (1992) and in "Pharmaprojects", PJB Publications Ltd.

As an example of the combination use, the modified TNFRI polypeptide or a fragment thereof in accordance with the present invention may be used in combination with first line drugs for control of inflammation, classified as non-steroidal, anti-inflammatory drugs (NSAIDs), for the treatment of TNF-mediated diseases, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis).

As another example of the combination use, the modified TNFRI polypeptide or a fragment thereof in accordance with the present invention may be used in combination with any of one or more slow-acting antirheumatic drugs (SAARDs) or disease modifying antirheumatic drugs (DMARDS), prodrug esters or pharmaceutically acceptable salts thereof, for the treatment of TNF-mediated diseases and multiple sclerosis as defined above.

As a further example of the combination use, the modified TNFRI polypeptide or a fragment thereof in accordance with the present invention may be used in combination with any of one or more COX2 inhibitors, prodrug esters or pharmaceutically acceptable salts thereof for the treatment of TNF-mediated diseases as defined above.

Further, the modified TNFRI polypeptide or a fragment thereof in accordance with the present invention may be used in combination with any of one or more antibacterial drugs, prodrug esters or pharmaceutically acceptable salts thereof for the treatment of TNF-mediated diseases as defined above.

The modified TNFRI polypeptide or a fragment thereof in accordance with the present invention may be used for the treatment of TNF-mediated diseases as defined above, in combination with any of one or more compounds given below: granulocyte colony stimulating factor; thalidomide; tenidap; tiapafant; nimesulide; panavir; rolipram; sulfasalazine; balsalazide; olsalazine; mesalazine; prednisolone; budesonide; methylprednisolone; hydrocortisone; methotrexate; cyclosporin; peptide T; (1R,3S)-cis-1-[9-(2,6-diaminopurinyl)]-3-hydroxy-4-cyclopentene hydrochloride; (1R, 3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

The modified TNFRI polypeptide or a fragment thereof in accordance with the present invention may be used in combination with one or more additional TNF inhibitors for the treatment of TNF-mediated diseases as defined above. Such TNF inhibitors include compounds and proteins which block in vivo synthesis or extracellular release of TNF: for example, anti-TNF antibodies including MAK 195F Fab antibody (Holler et al. (1993), 1st International Symposium on Cytokines in Bone Marrow Transplantation, 147); CDP 571 anti-TNF monoclonal antibody (Rankin et al. (1995), British Journal of Rheumatology, 34:334-342); BAY X 1351 murine anti-tumor necrosis factor monoclonal antibody (Kieft et al. (1995), 7th European Congress of Clinical Microbiology and Infectious Diseases, 9); CenTNF cA2 anti-TNF monoclonal antibody (Elliott et al. (1994), Lancet, 344:1125-1127 and Elliott et al. (1994), Lancet, 344:1105-1110).

Further, the present invention provides a pharmaceutical preparation containing the modified TNFRI polypeptide or a fragment thereof. Preferably, the pharmaceutical preparation of the present invention further contains a pharmaceutically acceptable excipients. The pharmaceutical preparation of the present invention may be in the form of a pharmaceutical formulation selected from the group consisting of an oral formulation, an inhaler, an injection, a transmucosal formulation, and an external application.

The pharmaceutical preparation of the present invention contains a therapeutically effective amount of a pharmaceutically acceptable diluent, preservative, solubilizer, emulsifier, adjuvant or carrier.

In addition, the pharmaceutical preparation of the present invention contains additives including buffer (e.g. Tris buffer, acetate buffer, or phosphate buffer), detergents (e.g. Tween®80), antioxidants (e.g. ascorbic acid, sodium metabisulfite), preservatives (e.g. Thimerosal, benzyl alcohol) and bulking substances (e.g. lactose, mannitol) which have been commonly used in the art. The additives may be incorporated into particulate preparations of polymeric compounds such as polylactic acid or polyglycolic acid or into liposomes. The pharmaceutical preparation of the present invention may contain hyaluronic acid for the purpose of promoting sustained duration in circulation. The pharmaceutical preparation of the present invention may optionally contain pharmaceutically acceptable liquid, semisolid, or solid diluents that serve as pharmaceutical vehicles, excipients, or media, including, but not being limited to, polyoxyethylene sorbitan monolaurate, starches, sucrose, dextrose, gum acacia, calcium phosphate, mineral oil, cocoa butter, and theobroma oil.

The pharmaceutical preparation of the present invention also contains inert additives which furnish protection against the stomach environment, and release of the biologically active material in the intestine.

The pharmaceutical preparation of the present invention is prepared using known techniques, including mixing, dissolving, granulating, dragee-making, levigating, emulsifying, encapsulating, entrapping or tabletting processes.

The pharmaceutical preparation of the present invention may be in the form of a liquid (e.g., a suspension, elixir and/or solution) or a solid (e.g., a powder, tablet and/or capsule), or may be formulated in the form of a depot. The depot preparation is typically longer acting than non-depot preparations. The depot preparation is prepared using suitable polymeric or hydrophobic materials (for example, an emulsion in a suitable oil) or ion exchange resins, or as sparingly soluble derivatives, for example, as a sparingly soluble salt. Further, the pharmaceutical preparation of the present invention contains a delivery system such as liposome or emulsion. Certain delivery systems are useful for preparing certain pharmaceutical preparations including those containing hydrophobic compounds. In certain embodiments, organic solvents such as dimethyl sulfoxide are used. In another aspect of the present invention, the pharmaceutical preparation of the present invention contains one or more tissue-specific delivery molecules designed to deliver pharmaceutical agents to specific tissues or cell types. For example, in certain embodiments, the pharmaceutical preparation contains a liposome coated with a tissue-specific antibody.

Preferably, the pharmaceutical preparation of the present invention may be formulated into an oral solid dosage form. Solid dosage forms include tablets, capsules, pills, troches or pellets.

Also, liposomal or proteinoid encapsulation may be used to formulate the composition of the present invention. Liposomes may be prepared from phospholipids, such as phosphatidylcholine (PC), phosphatidylethanolamine (PE), phosphatidic acid (PA), phosphatidylinositol (PI) or sphingomyelin (SM); and hydrophilic polymers, such as polyvinylpyrrolidone, polyvinylmethyl ether, polymethyl oxazoline, polyethyl oxazoline, polyhydroxypropyl oxazoline, polyhydroxypropyl methacrylamide, polymethacrylamide, polydimethylacrylamide, polyhydroxypropyl methacrylate, polyhydroxyethyl acrylate, hydroxymethyl cellulose, hydroxyethyl cellulose, polyethylene glycol and polyaspartamide.

If necessary, the modified TNFRI polypeptide or a fragment thereof contained in the pharmaceutical preparation of the present invention may be chemically modified so that oral delivery is efficacious. Generally, the chemical modification contemplated is the attachment of at least one moiety to the TNFRI variant polypeptide, where the moiety may be a substance which confers resistance to protease or helps uptake into the blood stream from the stomach or intestine. Preferably, the moiety for chemical modification may be a moiety for chemical modification to increase an overall stability of the pharmaceutical preparation of the present invention and therefore increase its circulation time in the body. Examples of the moiety include polyethylene glycol, copolymers of ethylene glycol and propylene glycol, carboxymethyl cellulose, dextran, polyvinyl alcohol, polyvinylpyrrolidone and polyproline. Other polymers that can be used are poly-1,3-dioxane and poly-1,3,6-trioxocane. Most preferred is a polyethylene glycol moiety (PEGylation).

As a carrier to enhance absorption of the pharmaceutical preparation of the present invention in the oral dosage form, a salt of a modified aliphatic amino acid, such as sodium N-(8-[2-hydroxybenzoyl]amino) caprylate (SNAC), may be used.

The pharmaceutical preparation of the present invention may be formulated as fine multiparticulates in the form of granules or pellets of a particle size of about 1 mm. In this case, the pharmaceutical may be in the form of a capsule. The multiparticulate preparation may be in the form of a powder, lightly compressed plug or tablet. The preparation may be prepared by compression.

The pharmaceutical preparation of the present invention may also be formulated in the form of, for example, liposome or microsphere encapsulation with further incorporation of colorants and flavoring agents.

Further, in order to enhance uptake of the modified TNFRI polypeptide or a fragment thereof which is an active ingredient in the pharmaceutical preparation of the present invention, additives may be used including fatty acids such as oleic acid or linoleic acid.

The pharmaceutical preparation of the present invention may be a controlled-release formulation. The TNFRI polypeptide or a fragment thereof, which is an active ingredient in such a formulation, may be incorporated into an inert carrier which permits controlled release by either diffusion or dissolution mechanisms. Further, the controlled-release formulation may contain a slowly disintegrating matrix, e.g., alginate or polysaccharide. Another form of the controlled-release formulation may be based on an Osmotic Release Oral delivery System (OROS®, Alza Corp.). In the controlled-release formulation, the TNFRI variant which is the active ingredient of the present invention is enclosed in a semi-permeable membrane which allows water to enter and push the active ingredient out through a single small opening due to osmotic effects. The controlled-release formulation of the present invention may have an enteric coating to exhibit a delayed release effect of the drug.

The pharmaceutical preparation of the present invention may be in the form of a film-coated tablet. The materials used in film coating are divided into two groups. The first group is a nonenteric material and includes methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, povidone and polyethylene glycol. The second group consists of enteric materials such as esters of phthalic acid. In detail, an enteric polymer as the enteric material is selected from the group consisting of an enteric cellulose derivative, an enteric acrylic copolymer, an enteric maleic copolymer, an enteric polyvinyl derivative, and a combination thereof. The enteric cellulose derivative is at least one selected from the group consisting of hypromellose acetate succinate, hypromellose phthalate, hydroxymethylethyl cellulose phthalate, cellulose acetate phthalate, cellulose acetate succinate, cellulose acetate maleate, cellulose benzoate phthalate, cellulose propionate phthalate, methylcellulose phthalate, carboxymethylethyl cellulose and ethylhydroxyethyl cellulose phthalate. The enteric acrylic copolymer is at least one selected from the group consisting of a styrene-acrylic acid copolymer, a methyl acrylate-acrylic acid copolymer, an acrylic acid-methyl methacrylate copolymer, a butyl acrylate-styrene-acrylic acid copolymer, a methacrylic acid-methyl methacrylate copolymer (e.g., Eudragit® L 100, Eudragit® S, Degussa), a methacrylic acid-ethyl acrylate copolymer (e.g., Eudragit® L 100-55, Degussa), and methyl acrylate-methacrylic acid-octyl acrylate copolymer. The enteric maleic copolymer is at least one selected from the group consisting of a vinyl acetate-maleic anhydride copolymer, a styrene-maleic anhydride copolymer, a styrene-maleic acid monoester copolymer, a vinylmethylether-maleic anhydride copolymer, an ethylene-maleic anhydride copolymer, a vinylbutylether-maleic anhydride copolymer, an acrylonitrile-methyl acrylate-maleic anhydride copolymer, and a butyl acrylate-styrene-maleic anhydride copolymer. The enteric polyvinyl derivative is at least one selected from the group consisting of polyvinylalcohol phthalate, polyvinylacetal phthalate, polyvinylbutyrate phthalate, and polyvinylacetacetal phthalate.

A mixture of the above-mentioned coating materials may be used to provide the optimum film coating. Film coating may be carried out in a pan coater or in a fluidized bed granulator or by a compression coater.

The controlled-release pharmaceutical preparation of the present invention may contain the modified TNFRI polypeptide of the present invention or a fragment thereof in a semi-permeable matrix of a solid hydrophobic polymer in the form of a shaped article, e.g., film or microcapsule, for the purpose of sustained release of the drug. Examples of the sustained-release matrix include polyesters, hydrogels [e.g., poly(2-hydroxyethyl-methacrylate) or poly(vinylalcohol) as described by Langer et al., J. Biomed. Mater. Res., 15:167-277, 1981 and Langer, Chem. Tech., 12:98-105, 1982], polylactides (U.S. Pat. No. 3,773,919, EP 58,481), copolymers of L-glutamic acid and gamma ethyl-L-glutamate (Sidman et al., Biopolymers 22:547-556, 1983), non-degradable ethylene-vinyl acetate (Langer et al., supra), degradable lactic acid-glycolic acid copolymers (e.g., Lupron Depot™ (injectable microspheres composed of lactic acid-glycolic acid copolymer and leuprolide acetate), and poly-D-(−)-3-hydroxybutyric acid (EP 133,988).

When encapsulated proteins remain in the body for a long time, they may denature or aggregate as a result of being exposed to moisture at 37° C., resulting in a loss of biological activity and possible changes in immunogenicity. Rational strategies can be devised for protein stabilization depending on the mechanism involved. For example, if the aggregation mechanism is discovered to form intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Further, the present invention provides a TNFRI variant of the present invention, and use of a pharmaceutical preparation containing the same. Such a pharmaceutical preparation may be administered via injection, or by oral, nasal, transdermal or other forms of administration, including, e.g., by intravenous, intradermal, intramuscular, intramammary, intraperitoneal, intrathecal, intraocular, intrapulmonary or subcutaneous injection; by sublingual, anal, vaginal, or by surgical implantation. The treatment may consist of a single dose or a plurality of doses over a period of time.

Further, the pharmaceutical preparation of the present invention may be delivered by a pulmonary delivery method. The pharmaceutical preparation of the present invention is delivered to the lung of a mammal while inhaling and traverses across the pulmonary epithelial lining to the blood stream.

A wide range of mechanical devices designed for pulmonary delivery of the drug may be used for pulmonary delivery of the pharmaceutical preparation of the present invention. Examples of such devices include nebulizers, metered dose inhalers, and powder inhalers, all of which are commercially available in the art.

The pharmaceutical preparation of the present invention may be appropriately formulated for optimum use in the foregoing devices. Typically, each formulation is specific to the type of device employed and may involve the use of an appropriate propellant, in addition to diluents, adjuvants or carriers useful in therapy.

The pharmaceutical preparation of the present invention for pulmonary delivery is preferably provided as a particulate form with an average particle size of approximately 10 μm or less, most preferably about 0.5 to 5 μm for effective delivery to the distal lung.

The pharmaceutical preparation of the present invention for pulmonary delivery may also contain a carbohydrate such as trehalose, mannitol, xylitol, sucrose, lactose or sorbitol, as a carrier. The pharmaceutical preparation may further contain dipalmitoylphosphatidylcholine (DPPC), dioleoylphosphatidyl ethanolamine (DOPE), distearoylphosphatidylcholine (DSPC) and dioleoylphosphatidylcholine (DOPC). The pharmaceutical preparation may also contain natural or synthetic surfactants. The pharmaceutical preparation may further contain polyethylene glycol, dextran such as cyclodextran, bile acid and other related derivatives, and amino acids used in a buffer formulation.

Also, the use of liposomes, microcapsules or microspheres, inclusion complexes, or other types of carriers is contemplated for pulmonary delivery of the pharmaceutical preparation of the present invention.

Pulmonary delivery of the pharmaceutical preparation of the present invention may be carried out using a nebulizer with either jet or ultrasonic means. The pharmaceutical preparation of the present invention suitable for use of a nebulizer contains the TNFRI variant dissolved in water at a concentration of about 0.1 to 500 mg per mL. The nebulizer formulation may also include a buffer and monosaccharides, which, for example, contributes to protein stabilization and the regulation of osmotic pressure. The nebulizer formulation may also contain a surfactant to reduce or prevent surface inducing aggregation of the protein caused by atomization of the solution in forming the aerosol.

The pharmaceutical preparation of the present invention for use with a metered-dose inhaler device will generally contain a finely divided powder of the composition containing the TNFRI variant of the present invention suspended in a propellant with the aid of a surfactant. The propellant may be a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or a combination thereof. Examples of a suitable surfactant that can be used herein include sorbitan trioleate and soya lecithin. Oleic acid may also be used as a surfactant.

The pharmaceutical preparation of the present invention for dispensing from a powder inhaler device is composed of a finely divided dry powder of the composition containing the TNFRI variant of the present invention and may also contain a bulking agent such as lactose, sorbitol, sucrose, mannitol, trehalose or xylitol. These may facilitate dispersion of the powder from the device.

Nasal delivery of the pharmaceutical preparation of the present invention is also contemplated. Nasal delivery allows the passage of a protein therapeutic to the blood stream directly after administering the protein therapeutic to the nose, thus preventing pulmonary deposition of the therapeutic product. The pharmaceutical preparation of the present invention for nasal delivery contains dextran or cyclodextran, etc. Delivery via transport across other mucous membranes is also contemplated for the pharmaceutical preparation of the present invention.

The dosage regimen of the pharmaceutical preparation of the present invention involved in a method for treating the above-described diseases or conditions will be determined by the attending physician, in light of various factors which modify the action of drugs, e.g. the age, condition, body weight, sex and diet of the patient, the severity of any infection, the time of administration and other clinical factors.

The pharmaceutical preparation of the present invention may be administered via single dosing or continuous dosing, but is preferably administered by an initial bolus followed by a continuous infusion to maintain therapeutic levels of the drug in circulation. Typical techniques known in the art will readily optimize effective dosages and administration regimens. The frequency of dosing will depend on the pharmacokinetic parameters of the agents and the route of administration. The dosage regimen, administration regimen and frequency of dosing may also be optimized according to the physical state, stability, rate of in vivo release, and rate of in vivo clearance of the administered agents. For each route of administration, a suitable dose may be calculated according to body weight, body surface area or organ size. Appropriate dosages may be ascertained due to established assays used for determining blood level dosages in conjunction with appropriate dose-response data. The final dosage regimen will be determined by the attending physician, in light of various factors which modify the action of drugs, e.g. the drug's specific activity, the severity and the responsiveness of the patient, the age, condition, body weight, sex and diet of the patient and other clinical factors. As studies are conducted, further information will emerge regarding the appropriate dosage levels and duration of treatment for various diseases and conditions.

Advantageous Effects

The modified human tumor necrosis factor receptor-I (TNFRI) polypeptide or a fragment thereof in accordance with the present invention has improved binding affinity to the TNF comparing to the natural TNFRI. Therefore, it can be used as protein agent for effectively inhibiting an activity of TNF.

DESCRIPTION OF THE DRAWINGS

FIG. 1 is a schematic diagram showing the construction of an *E. coli* expression vector capable of expressing Met-TNFRI105, Met-TNFRI126, or Met-TNFRI171 by inserting a gene encoding Met-TNFRI105, Met-TNFRI126, or Met-TNFRI171 into a pET44a.

FIG. 2A is a view confirming elution of Met-TNFRI105, Met-TNFRI126 and Met-TNFRI171 protein by gel filtration chromatogram (fraction A4), and FIG. 2B is a photograph showing the SDS-PAGE silver staining) analysis results of purified Met-TNFRI105, Met-TNFRI126 and Met-TNFRI171 under the non-reduced state.

FIG. 3 is a graph confirming the binding ability of TNFRI fragments (TNFRI126, TNFRI171) and TNFRI variant fragments (TNFRI126-30, TNFRI171-30) to the TNF-α by ELISA analysis FIG. 4 is a graph confirming the binding ability of TNFRI fragments (TNFRI171) and TNFRI variant fragments (TNFRI171-9, TNFRI171-26) to the TNF-α by ELISA analysis FIG. 5 is a graph confirming the binding ability of TNFRI fragments (TNFRI171) and TNFRI variant fragments (TNFRI171-25, TNFRI171-26) to the TNF-α by ELISA analysis FIG. 6 is a graph confirming the biological activity of TNFRI fragments (TNFRI126, TNFRI171) and TNFRI variant fragments (TNFRI126-30, TNFRI171-30) by cell cytotoxicity assay.

FIG. 7 is a graph confirming the biological activity of ENBREL™, TNFRI fragment (TNFRI171) and TNFRI variant fragments (TNFRI171-2, TNFRI171-8, TNFRI171-9) by cell cytotoxicity assay.

FIG. 8 is a graph confirming the biological activity of ENBREL™, TNFRI fragment (TNFRI171) and TNFRI variant fragments (TNFRI171-10, TNFRI171-15, TNFRI171-16) by cell cytotoxicity assay.

FIG. 9 is a graph confirming the biological activity of ENBREL™, TNFRI fragment (TNFRI171) and TNFRI variant fragments (TNFRI171-18, TNFRI171-21, TNFRI171-22) by cell cytotoxicity assay.

BEST MODE FOR INVENTION

The above and other objects, features and other advantages of the present invention will be more clearly understood from the following Examples. However, the present invention is not limited to the examples disclosed below.

The TNFRI polypeptide or a fragment thereof in accordance with the present invention was prepared using information of a human TNFRI genome whose genome has been already publicly disclosed.

PREPARATION EXAMPLE

Preparation of TNFRI Fragments

(1) Preparation of TNFRI Gene Fragment: Preparation of TNFRI171

It is reported that human TNFRI has 4 extracellular domains, binding of TNFRI to TNF-α is possible even with only three domains of TNFRI (TNFRI126), and more deficiency of the extracellular domains has no effect on the binding of TNFRI to TNF-α. Based on this fact, TNFRI171 having 171 amino acid residues extending from amino acid residue 41 of the human TNFRI polypeptide as set forth in SEQ ID NO: 1, TNFRI126 having 126 amino acid residues extending from amino acid residue 41 of human TNFRI, and TNFRI105 having 105 amino acid residues extending from amino acid residue 41 of human TNFRI were selected as candidate peptides for constructing variants of the present invention. For producing such variants, the nucleotide sequence of TNFRI171 was modified to be convenient for expression in *E. coli*, using codons optimized in *E. coli* (SEQ ID NO: 5). This sequence was constructed by PCR-based gene synthesis method.

In order to insert the synthesized gene sequence into a pGEM®-T (Cat. No: A1380, Promega) vector, 3 μl of the synthetic gene was added to 1 μl of the pGEM®-T vector, and 1 μl of ligase (Cat. No: M2200S, NEB) and a ligation solution (2× ligation buffer) were added thereto, followed by reaction at room temperature for 10 minutes. 2 μl of the reaction solution was taken and added to an XL1-blue competent cell (Cat. No: RH119-J80, RBC) which was then transformed by applying heat shock at 37° C. for 2 minutes, followed by static culture in an LB solid medium containing ampicillin to obtain a colony. The colony was cultured in an LB liquid medium containing ampicillin, the plasmid was isolated therefrom and the gene sequence was confirmed by fluorescence-labeling of ddNTP using PCR (SolGent™, SolGent Inc., South Korea). This gene was designated as pGEM-TNFRI171. Hereinafter, TNFRI126 and TNFRI105 genes other than TNFRI171 were obtained by PCR using the above-obtained pGEM-TNFRI171 gene as a template.

(2) Preparation of TNFRI Expression Vector: Preparation of TNFRI105, TNFRI126, TNFRI171 Expression Vector In order to expression of Met-TNFRI (TNFRI starting from Met) in *E. Coli*, constructed expression vector by using commercially available pET44a vector (Novagen, Cat. No:71122-3).

More specifically, Met-TNFRI105 gene (SEQ ID NO:6) was obtained by PCR synthesis by using pGEM-TNFRI171 as a template. At the time, NdeI and HindIII restriction enzyme recognition sites were inserted at 5' end and 3' end, respectively, for cloning to pET44a vector.

```
Primer sequence for PCT amplification are:
                                       SEQ ID NO 161
Forward primer:   5'-acatatggatagcgtgtgcccgc-3'

SEQ ID NO 162
Backward primer:  5'-taagcttattaattaaaacactggaac-3'
```

PCR was carried out including: primary denaturation at 95° C. for 5 minutes, secondary denaturation at 95° C. for 1 minute, primer annealing at 60° C. for 40 seconds and elongation at 72° C. for 1 minutes. The process described above, steps of from secondary denaturation to elongation was repeated 25 times (25 cycles) and then the final enzymatic reaction at 72° C. for 10 minutes.

Restriction enzymes (NdeI and HindIII) were added to the amplified gene and pET44a vector, and reacted at 37° C. for 3 hours. After treatment with restriction enzyme, 1% agarose gel electrophoresis was carried out. The targeted gene was obtained by using DNA extraction kit (GeneAll®, Cat. No:102-102) from DNA band obtained by blade cutting.

50 ng of pET44a vector, 200 ng of Met-TNFRI105 gene, and 10 μl of 2× ligation premix (NEB, Cat. No: M2200S) were added, and sterilized distilled water was added to make final volume of 20 μl. The reaction was carried out 25° C. for 5 minutes.

2 μl of the reacted solution was added to BL21Star™(DE3) (Invitrogen™, Cat. NO:C6010-03) competent cell, and then transformed by applying heat shock at 37° C. for 2 minutes, followed by static culture in an LB solid medium containing ampicillin to obtain a colony.

The colony was cultured in an LB liquid medium containing ampicillin, the plasmid was isolated therefrom and the gene sequence was confirmed sequence analysis. This plasmid was designated as pET44A-Met-TNFRI105 (FIG. 1).

Met-TNFRI126 gene (SEQ ID NO:7) was obtained by PCR synthesis by using pGEM-TNFRI171 as a template. At the time, NdeI and BamHI restriction enzyme recognition sites were inserted at 5' end and 3' end, respectively, for cloning to pET44a vector.

```
Primer sequence for PCT amplification are:
                                       SEQ ID NO 163
Forward primer:   5'-acatatggatagcgtgtgcccgc-3'

SEQ ID NO 164
Backward primer: 5'-cggatccttaacaaactgtattctgcttc-3'
```

The PCR reaction protocol was same with the above mentioned method used to obtain Met-TNFRI105 gene, and the protocol for construction of expression vector for *E. coli* was also same with the above mentioned method used to obtain Met-TNFRI105 vector, except that NdeI and BamHI restriction enzyme were used.

The plasmid was designated as pET44a-Met-TNFRI126, and completion of cloning was confirmed by gene sequence analysis in the plasmid from the colony (FIG. 1).

Met-TNFRI171 gene (SEQ ID NO:8) was obtained by PCR synthesis by using pGEM-TNFRI1171 as a template. At the time, NdeI and BamHI restriction enzyme recognition sites were inserted at 5' end and 3' end, respectively, for cloning to pET44a vector.

```
Primer sequence for PCT amplification are:
                                       SEQ ID NO 165
Forward primer:   5'-acatatggatagcgtgtgcccgc-3'

SEQ ID NO 166
Backward primer: 5'-cggatccttatgtggtgcctgagtcctc-3'
```

The protocol for PCR reaction and construction of expression vector for *E. coli* was same with the above mentioned method used to obtain Met-TNFRI126.

The plasmid was designated as pET44a-Met-TNFRI126, and completion of cloning was confirmed by gene sequence analysis in the plasmid from the colony (FIG. 1).

Example 1

Preparation of TNFRI Fragment Mutant (1) Design of TNFRI Mutant

A list of amino acid modifications to be applied to TNFRI105, TNFRI126, and TNFRI171 was shown in Table 1. TNFRI amino acid modification for improving affinity was designed by a method of analyzing sites of amino acids expected to be involved in binding to TNF-α through a structure of TNFRI on a wild-type human TNFRI amino acid sequence disclosed in sequence number 1 and substituting amino acid with other amino acids at each site so as to increase the affinity.

Mutants in which amino acid modifications shown in No. 1 to 30 of Table 1 were introduced in TNFRI105, TNFRI126, and TNFRI171, respectively, were referred to as TNFRI105-1 to TNFRI105-30 (sequence number 9 to 38), TNFRI126-1 to TNFRI126-30 (sequence number 39 to 68), and TNFRI171-1 to TNFRI171-30 (sequence number 69 to 98).

(2) Preparation of DNA Coding TNFRI Mutants

In order to prepare a site specific TNFRI mutant, TNFRI mutants were prepared by a site-directed mutagenesis method. Primers used to prepare the TNFRI mutant including thirty kinds of amino acid modifications shown in Table 1 were shown in the following Table 2.

TABLE 1

List of designed TNFRI amino acid modification

| No. | The position and type of amino acid modification |
|---|---|
| #1 | H95F, R97P, H98A |
| #2 | S92I, H95F, R97P, H98A |
| #3 | S92G, H95F, R97P, H98A |
| #4 | S92A, H95F, R97P, H98A |
| #5 | S92V, H95F, R97P, H98A |
| #6 | S92L, H95F, R97P, H98A |
| #7 | S92P, H95F, R97P, H98A |
| #8 | S92F, H95F, R97P, H98A |
| #9 | S92M, H95F, R97P, H98A |
| #10 | S92W, H95F, R97P, H98A |
| #11 | S92C, H95F, R97P, H98A |
| #12 | S92N, H95F, R97P, H98A |
| #13 | S92Q, H95F, R97P, H98A |
| #14 | S92T, H95F, R97P, H98A |
| #15 | S92Y, H95F, R97P, H98A |
| #16 | S92K, H95F, R97P, H98A |
| #17 | S92R, H95F, R97P, H98A |
| #18 | S92H, H95F, R97P, H98A |
| #19 | S92D, H95F, R97P, H98A |
| #20 | S92E, H95F, R97P, H98A |
| #21 | S92I, H95F, R97P, H98G |
| #22 | S92M, H95F, R97P, H98G |
| #23 | S92I, E93P, H95F, R97I, H98A |

TABLE 1-continued

List of designed TNFRI amino acid modification

| No. | The position and type of amino acid modification |
|---|---|
| #24 | S92I, E93P, H95F, R97I, H98A |
| #25 | S92I, E93P, H95F, R97F, H98A |
| #26 | S92I, E93P, H95F, R97P, H98G |
| #27 | S92I, E93P, H95F, R97L, H98G |
| #28 | S92I, E93P, H95F, R97I, H98G |
| #29 | S92I, E93P, H95F, R97F, H98G |
| #30 | S92I, E93P, H95F, R97P, H98A |

More specifically, TNFRI (the above-prepared pE44a-TNFRI105, pET44a-TNFRI126, or pE44a-TNFRI171) plasmid was used as a template, and each pair of primers of the following Table 2 were dissolved in distilled water so as to have a concentration of 20 pmole. Then, a PCR reaction using a Pfu polymerase was carried out, thereby preparing the site specific mutant. Plasmids coding TNFRI (105, 126, and 171)-1 and TNFRI (105, 126, and 171)-30, respectively, were prepared using the above-prepared pE44a-TNFRI105, pET44a-TNFRI126, or pE44a-TNFRI171 plasmid as a template and the #1 and #3 primer of the following Table 2 (referred to as pET-TNFRI (105, 126, and 171)_1 and pET-TNFRI (105, 126, and 171)_30, respectively). As shown in the following Table 2, pET-TNFRI_2 to pET-TNFRI_29 were prepared using the plasmid prepared as described above as the template.

A composition of a solution used for PCR was as follows: each of the template plasmids DNA (1 µl), 20 pmole N-primer (1 µl), 20 pmole C-primer (1 µl), 2× primeSTAR PCR buffer (25 µl), 200 µM dNTP (4 µl), PrimeSTAR HS DNA polymerase (Takara, Cat. No: R044A, 0.5 µl), and distilled water (17.5 µl) were added to thereby prepare the reaction solution (50 µl).

The PCR was carried out by repeatedly performing an extension reaction 17 times in a secondary modification process among a primary modification process at 98° C. for 5 minutes, a secondary modification process at 98° C. for 30 seconds, a primer adhesion process at 55° C. for 30 seconds, and an extension reaction process at 72° C. for 9 minutes and then performing a final enzyme reaction at 72° C. for 10 minutes, thereby completing the reaction.

The PCR product was treated with Dpn I enzyme at 37° C. for 2 hours to dissolve DNA derived from *E. Coli*, and DNA amplified by the PCR was secured. 2 µl of DNA solution was extracted and injected into XL1-blue competent cells (RBC, Cat. No: RH119-J180). Then, heat shock was applied thereto at 42° C. for 1 minute to transform the cell and then static-cultured in a LB solid culture medium containing ampicillin, thereby obtaining a colony. After this colony was cultured in a LB liquid culture medium containing ampicillin, plasmid was separated, and completion of the site specific mutant was confirmed by base sequence analysis.

TABLE 2

Primer for inducing site specific mutant

| No. | PCR template | Primer sequences |
|---|---|---|
| #30 | pET44a-Met-TNFRI105, | 5'-GAGTGGGTCATTTACAGCGATTCCGAATTTTCTGCCGGCGTGCCTGAGCTGTTCTAAG-3' SEQ ID NO 99 |
|  | pET44a-Met-TNFRI120, or pET44a-Met-TNFRI171 | 5'-CTTAGAACAGCTCAGGCACGCCGGCAGAAAATTCGGAATCGCTGTAAATGACCCACTC-3' SEQ ID NO 100 |
| #1 | pET44a-Met-TNFRI105, | 1st PCR |
|  | pET44a-Met-TNFRI126, or pET44a-Met-TNFRI171 | 5'-CATTTACAGCGAGTGAGAATTTTCTGCGCGCGTGCCTGAGCTGTTCTAAG-3' SEQ ID NO 101<br>5'-CTTAGAACAGCTGAGGCACGCGCGCAGAAAATTCTCACTCGCTGGAAATG-3' SEQ ID NO 102<br>2nd PCR |
|  |  | 5'-GAGTGAGAATTTTCTGCCGGCGTGCCTGAGCTGT-3' SEQ ID NO 103<br>5'-ACAGCTCAGGCACGCCGGCAGAAAATTCTCACTC-3' SEQ ID NO 104 |
| #2 | pET-TNFRI_30 | 5'-GTCATTTACAGCGATTGAGAATTTTCTGCCGGC-3' SEQ ID NO 105<br>5'-GCCGGCAGAAAATTCTCAATCGCTGTAAATGAC-3' SEQ ID NO 106 |
| #3 | pET-TNFRI_2 | 5'-GGGTCATTTAGAGCGGGGGAGAATTTTCTGC-3' SEQ ID NO 107<br>5'-GCAGAAAATTCTCCCCCGCTGTAAATGACCC-3' SEQ ID NO 108 |
| #4 | pET-TNFRI_2 | 5'-GGGTCATTTACAGCGGCGGAGAATTTTCTGC-3' SEQ ID NO 109<br>5'-GCAGAAAATTCTCCGCCGCTGTAAATGACCC-3' SEQ ID NO 110 |
| #5 | pET-TNFRI_2 | 5'-GGGTCATTTACAGCGGTTGAGAATTTTCTGC-3' SEQ ID NO 111<br>5'-GCAGAAAATTCTCAACCGCTGTAAATGACCC-3' SEQ ID NO 112 |
| #6 | pET-TNFRI_2 | 5'-GGGTCATTTACAGCGGTGGAGAATTTTCTGC-3' SEQ ID NO 113<br>5'-GCAGAAAATTCTCCAGCGCTGTAAATGACCC-3' SEQ ID NO 114 |
| #7 | pET-TNFRI_2 | 5'-GGGTCATTTACAGCGCCGGAGAATTTTCTGG-3' SEQ ID NO 115<br>5'-GCAGAAAATTCTCCGGCGCTGTAAATGACCC-3' SEQ ID NO 116 |
| #8 | pET-TNFRI_2 | 5'-GGGTCATTTACAGCGTTTGAGAATTTTCTGC-3' SEQ ID NO 117<br>5'-GCAGAAAATTCTCAAACGCTGTAAATGACCC-3' SEQ ID NO 118 |

TABLE 2-continued

Primer for inducing site specific mutant

| No. | PCR template | Primer sequences | |
|---|---|---|---|
| #9 | pET-TNFRI_2 | 5'-GGGTCATTTACAGCGATGGAGAATTTTCTGC-3' | SEQ ID NO 119 |
| | | 5'-GCAGAAAATTCTCCATCGCTGTAAATGACCC-3' | SEQ ID NO 120 |
| #10 | pET-TNFRI_2 | 5'-GGGTCATTTACAGCGTGGGAGAATTTTCTGC-3' | SEQ ID NO 121 |
| | | 5'-GCAGAAAATTCTCCCACGCTGTAAATGACCC-3' | SEQ ID NO 122 |
| #11 | pET-TNFRI_2 | 5'-GGGTCATTTACAGCGTGCCAGAATTTTCTGC-3' | SEQ ID NO 123 |
| | | 5'-GCAGAAAATTCTCGCACGCTGTAAATGACCC-3' | SEQ ID NO 124 |
| #12 | PET-TNFRI_2 | 5'-GGGTCATTTACAGCGAATGAGAATTTTCTGC-3' | SEQ ID NO 125 |
| | | 5'-GCAGAAAATTCTCATTCGCTGTAAATGACCC-3' | SEQ ID NO 126 |
| #13 | pET-TNFRI_2 | 5'-GGGTCATTTACAGCGCAGGAGAATTTTCTGC-3' | SEQ ID NO 127 |
| | | 5'-GCAGAAAATTCTCCTGCGCTGTAAATGACCC-3' | SEQ ID NO 128 |
| #14 | pET-TNFRI_2 | 5'-GGGTCATTTACAGCGACAGAGAATTTTCTGC-3' | SEQ ID NO 129 |
| | | 5'-GCAGAAAATTCTCTGTCGCTGTAAATGACCC-3' | SEQ ID NO 130 |
| #15 | pET-TNFRI_2 | 5'-GGGTCATTTACAGCGTACGAGAATTTTCTGC-3' | SEQ ID NO 131 |
| | | 5'-GCAGAAAATTCTCGTACGCTGTAAATGACCC-3' | SEQ ID NO 132 |
| #16 | pET-TNFRI_2 | 5'-GGGTCATTTACAGCGAAGGAGAATTTGTGC-3' | SEQ ID NO 133 |
| | | 5'-GCAGAAAATTCTCCTTCGCTGTAAATGACCC-3' | SEQ ID NO 134 |
| #17 | pET-TNFRI_2 | 5'-GGGTCATTTACAGCGCGCGAGAATTTTCTGC-3' | SEQ ID NO 135 |
| | | 5'-GCAGAAAATTCTCGCGCGCTGTAAATGACCC-3' | SEQ ID NO 136 |
| #18 | pET-TNFRI_2 | 5'-GGGTCATTTACAGCGCATGAGAATTTTCTGC-3' | SEQ ID NO 137 |
| | | 5'-GCAGAAAATTCTCATGCGCTGTAAATGACCC-3' | SEQ ID NO 138 |
| #19 | pET-TNFRI_2 | 5'-GGGTCATTTACAGCGGATGAGAATTTTCTGC-3' | SEQ ID NO 139 |
| | | 5'-GCAGAAAATTCTCATCCGCTGTAAATGAGCC-3' | SEQ ID NO 140 |
| #20 | pET-TNFRI_2 | 5'-GGGTCATTTACAGCGGAAGAGAATTTTCTGC-3' | SEQ ID NO 141 |
| | | 5'-GCAGAAAATTCTCTTCCGCTGTAAATGACCC-3' | SEQ ID NO 142 |
| #21 | pET-TNFRI_2 | 5'-GAGAATTTTCTGGCGGGGTGCCTGAGCTGTTCTA-3' | SEQ ID NO 143 |
| | | 5'-TAGAACAGCTCAGGCACCCCGGCAGAAAATTCTC-3' | SEQ ID NO 144 |
| #22 | pET-TNFRI_9 | 5'-GAGAATTTTCTGCCGGGGTGCCTGAGCTGTTCTA-3' | SEQ ID NO 145 |
| | | 5'-TAGAACAGCTCAGGCACCCCGGCAGAAAATTCTC-3' | SEQ ID NO 146 |
| #23 | pET-TNFRI_30 | 5'-GATTCCCAATTTTCTGCTGGCGTGCCTGAGCTGT-3' | SEQ ID NO 147 |
| | | 5'-ACAGCTCAGGCACGCCAGCAGAAAATTCGGAATC-3' | SEQ ID NO 148 |
| #24 | pET-TNFRI_30 | 5'-GATTCCGAATTTTCTGATTGCGTGCCTGAGCTGT-3' | SEQ ID NO 149 |
| | | 5'-ACAGCTCAGGCACGCAATCAGAAAATTCGGAATC-3' | SEQ ID NO 150 |
| #25 | pET-TNFRI_30 | 5'-GATTCCGAATTTTCTGTTTGCGTGCCTGAGCTGT-3' | SEQ ID NO 151 |
| | | 5'-ACAGCTCAGGCACGCAAACAGAAAATTCGGAATC-3' | SEQ ID NO 152 |
| #26 | pET-TNFRI_30 | 5'-TCCGAATTTTCTGCCGGGGTGCCTGAGCTGTTC-3' | SEQ ID NO 153 |
| | | 5'-GAACAGCTCAGGCACCCCGGCAGAAAATTCGGA-3' | SEQ ID NO 154 |
| #27 | pET-TNFRI_30 | 5'-AGCGATTCCGAATTTTCTGCTGGGGTGCCTGAGCTGTTCTAAG-3' | SEQ ID NO 155 |
| | | 5'-CTTAGAACAGCTCAGGCACCCCAGCAGAAAATTCGGAATCGCT-3' | SEQ ID NO 156 |
| #28 | pET-TNFRI_30 | 5'-AGCGATTCCGAATTTTCTGATTGGGTGCCTGAGCTGTTCTAAG-3' | SEQ ID NO 157 |
| | | 5'-CTTAGAACAGCTCAGGCACCCAATCAGAAAATTCGGAATCGCT-3' | SEQ ID NO 158 |
| #29 | pET-TNFRI_30 | 5'-AGCGATTCCGAATTTTCTGTTTGGGTGCCTGAGCTGTTCTAAG-3' | SEQ ID NO 159 |
| | | 5'-CTTAGAACAGCTCAGGCACCCAAACAGAAAATTCGGAATCGCT-3' | SEQ ID NO 160 |

(3) Production of Biological Active Met-TNFRI and Met-TNFRI Mutants in *E. coli*

(a) Expression of Met-TNFRI and Met-TNFRI Mutants

1 μl of the above-prepared plasmid solution was extracted and injected into BL21Star™(DE3) (Invitrogen™, Cat. No: C6010-03) competent cells. Then, heat shock was applied thereto at 42° C. for 1 minute to transform the cell and then static-cultured in a LB solid culture medium containing ampicillin, thereby obtaining a colony. The *E. coli* BL21Star™ (DE3) anchoring the expression vector therein was inoculated into 50 mL of YP culture medium (yeast extract: Merck, Cat. No: 103753, peptone: BD, Cat. No: 243620, NaCl: Merck, Cat. No: 1064049025) containing ampicillin (100 μg/mL)

and cultured at 37° C. for 16 hours with aeration. The culture was inoculated into 250 mL of YP culture medium containing ampicillin (100 µg/ml) in a 1 L flask so that absorbance is 0.1 at 600 nm. When the cells were grown at 37° C. to have the absorbance of 3 to 4 at 600 nm, IPTG was added at a final concentration of 1.0 mM to induce expression. After IPTG induction, the cells were further cultured at 37° C. for 3 hours with aeration and collected by centrifugation at 6000 rpm for 20 minutes.

(b) Recovery of Insoluble Met-TNFRI and Met-TNFRI Mutants

The collected cells were re-suspended in a re-suspension solution (50 mM Tris, 0.5 mM EDTA, pH 8.5) and disrupted with a sonicator (Sonics, Cat. No: VCX 750). After cell disruption, centrifugation at 8000×g and 10° C. for 30 minutes was performed, and then the supernatant was discarded and the precipitated pellet was suspended in a pellet washing solution 1 (35 mL, 50 mM Tris, 10 mM EDTA, 0.5% Triton™ X-100, pH 8.0) and centrifuged at 8000×g and 10° C. for 20 minutes. The supernatant was discarded and the resulting pellet was re-suspended in a re-suspension solution (35 mL) and centrifuged at 8000×g and 10° C. for 20 minutes. The pellet was used immediately or freeze-stored at −80° C. until use.

(c) Solubilization and Refolding of Met-TNFRI and Met-TNFRI Mutants

The pellet was completely solubilized in 6 mL of a denaturation solution (6 to 8 M urea or 6 to 8 M guanidine-HCl, 10 mM dithiothreitol (DTT), 2.0 mM EDTA, 0.2 M NaCl). The insoluble part of the pellet was filtered off through a 0.45 µm syringe filter. The pellet-solubilized solution was 20-fold diluted in a refolding solution (50 mM Tris, 1.0 mM EDTA, 0.5 M L-arginine, 6.0 mM GSH, 4.0 mM GSSG, 240 mM NaCl, 10 mM KCl, pH 9.0) and gently stirred at 4° C. for 12 to 24 hours to induce refolding.

(d) Purification of Refolded Met-TNFRI and Met-TNFRI Mutants

In order to purify the refolded Met-TNFRI and Met-TNFRI mutants, the refolding solutions were 20-fold concentrated using a 3 kD Amicon® Ultra (Millipore, Cat. No: UFC900324), followed by gel filtration chromatography using a Superdex® 75 prep grade resin (GE)-packed XK50/60 column (GE, Cat. No: 18-8752-01).

Figure 2:
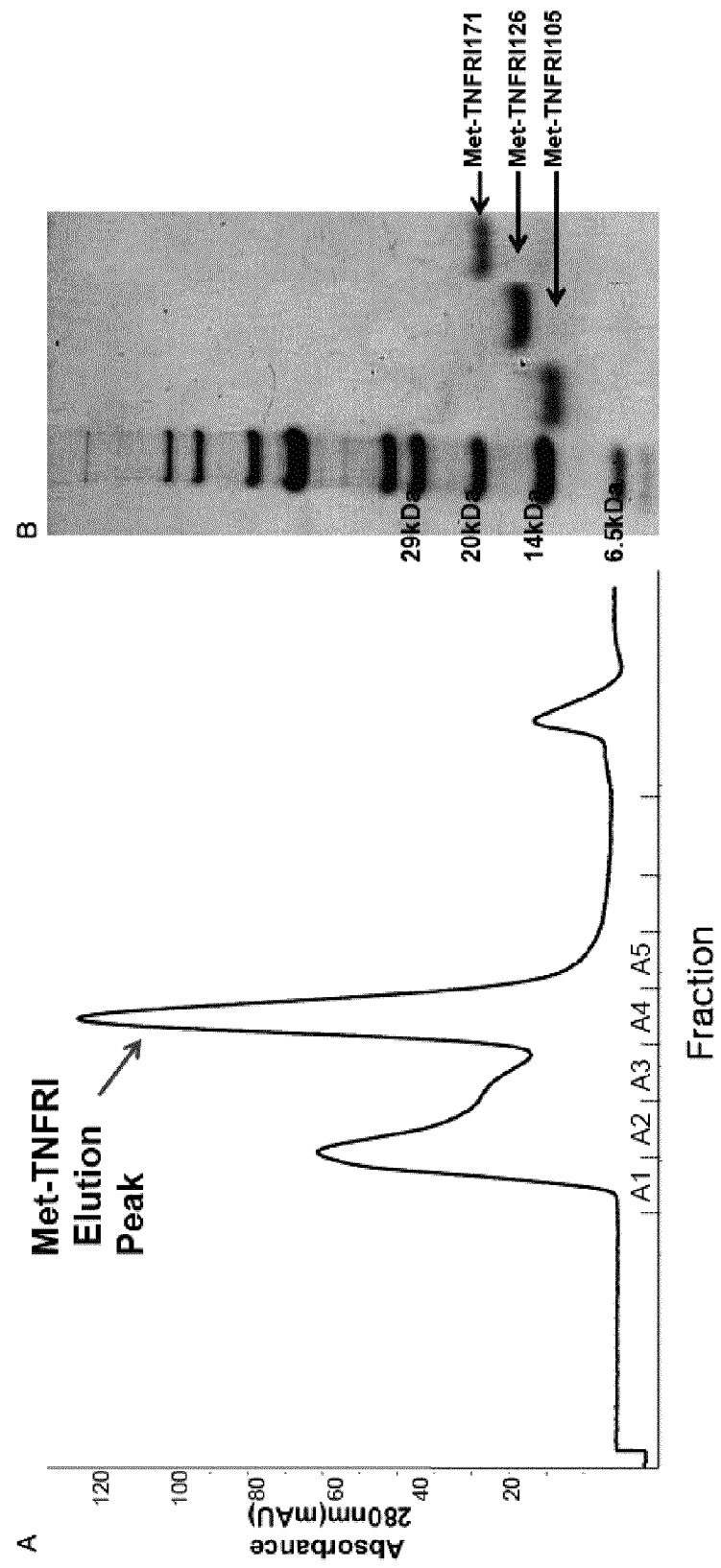
Figure 3:
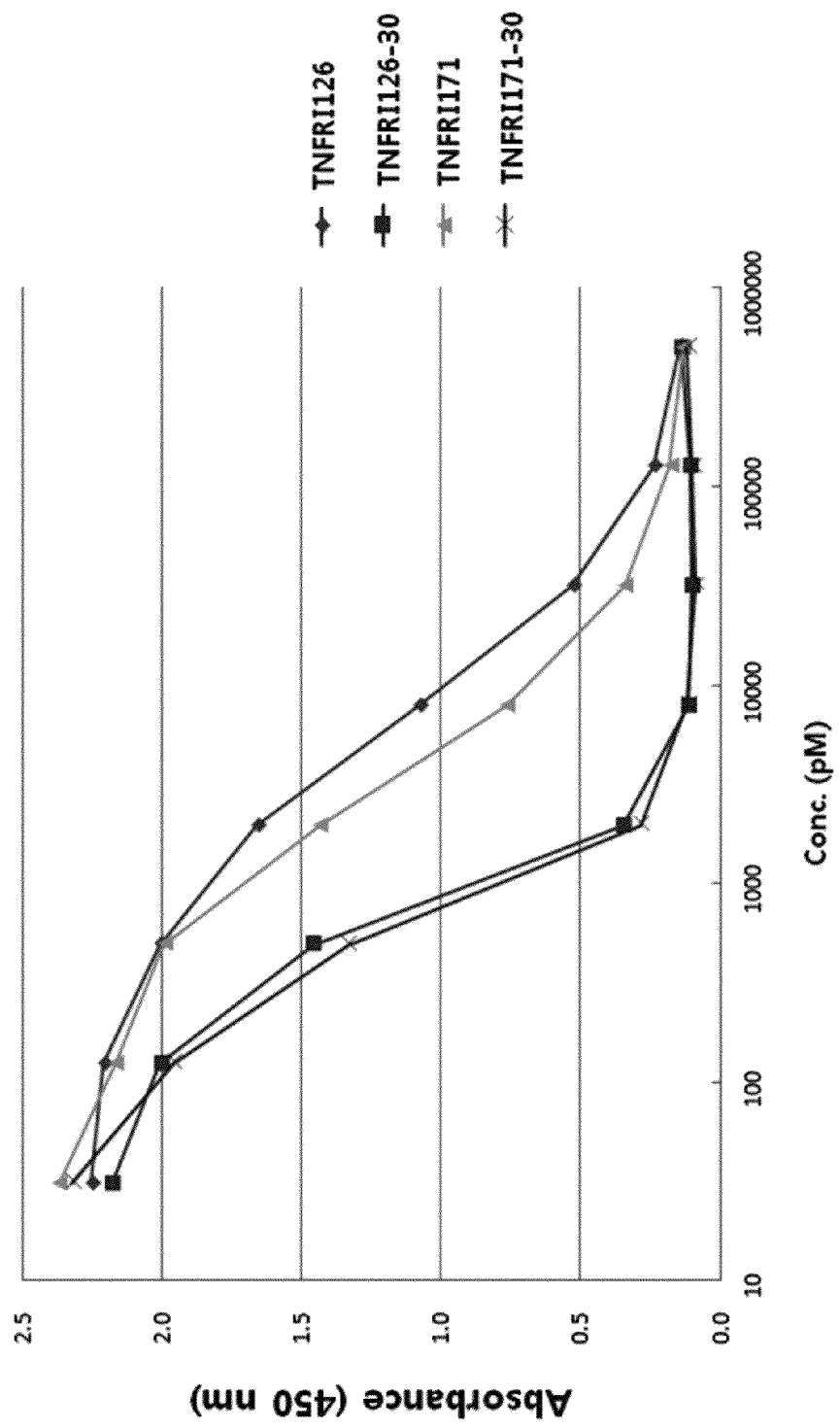

More specifically, before the refolded sample was loaded onto the column, the column was equilibrated with 4-5 column volumes of an equilibration solution (50 mM sodium phosphate, 100 mM NaCl, and pH 7.0). After 250 µL of the sample was loaded onto the column, the equilibration solution was allowed to flow through the column at a flow rate of 0.5 mL/min and 2.0 mL fractions were taken. After the taken sample in the fraction was analyzed by SDS-PAGE, only the fractions having a purity of 90% or more were used. Through this procedure, Met-TNFRI105, Met-TNFRI126, Met-TNFRI171, a Met-TNFRI105 mutant, a Met-TNFRI126 mutant and a Met-TNFRI171 mutant were purified (FIG. 2).

Experimental Example 1

Confirmation of Affinity of Met-TNFRI for the Ligand (TNF-α)

The Met-TNFRI and the Met-TNFRI mutant that have a purity of 90% or more were quantified using a Bradford method, and the affinity for TNF-α was measured using an ELISA assay.

100 µL of TNFRI190 (proteins consisting of 190 amino acid residues extending from position 22 to position 211 in the amino acid sequence of TNFRI of a sequence number 1, R&D, Cat. No: 636-R1-025-CF) was loaded at a concentration of 1 µg/ml into 96-well plates and immobilized at 4° C. for 16 hours. Each well was washed three times with 300 µL of washing solution (0.05% Tween-20, PBS, pH 7.4), and 300 µL of a blocking solution (5% skim milk, PBS, pH 7.4) was added thereto to perform a reaction at room temperature for 2 hours. Then, each well was washed as described above. A sample to be analyzed was diluted to concentrations of 500 nM, 125 nM, 31 nM, 7.8 nM, 1.9 nM, 0.48 nM, 0.12 nM, and 0.03 nM in series and loaded in an amount of 100 µL into each well in duplicate. 100 µL of 50 ng/ml TNF-α was added to each well, followed by performing the reaction at room temperature for 2 hours. After the wells were washed with a washing solution, 100 µg/mL TNF-α antibody solution (Abcam, Cat. NO. ab9642) was diluted to 1/1000 and added in the amount of 100 µL per each well to perform the reaction at room temperature for 2 hours. After the plates were washed with a washing solution, a substrate solution was added in an amount of 100 µL to each well and reacted at room temperature for 15 minutes. In each well, 100 µL of 3,3',5,5'-tetramethylbenzidine (RnD, Cat. No: DY999), that is the substrate solution, was injected to perform the reaction at room temperature for 15 minutes, followed by adding 50 µL of 1.0 M sulfuric acid (Samchun Chemical, Cat. No: S2129) to each well to stop the reaction. Absorbance at 450 and 540 nm was read on a Vmax reader (MD, Model: VersaMax).

The affinity of Met-TNFRI and Met-TNFRI mutants for TNF-α was determined by measuring an absorbance change according to the concentration and evaluating IC50 value by measuring an absorbance change according to the concentration. The affinity of Met-TNFRI mutant relative to the wild-type TNFRI was determined therefrom. The results were shown in the following Table 3. In addition, data of the representative mutants (TNFRI126-30, TNFRI171-9, TNFRI171-10, TNFRI171-25, TNFRI171-26, TNFRI171-30) were shown in FIGS. 3 and 5. Particularly, as shown in FIG. 3, it was confirmed that TNFRI126 and TNFRI171 have substantially the same effect. In addition, as shown in FIG. 3, the TNFRI mutants according the present invention exhibited affinity improved by at most 1,400% compared to that of the wild-type TNFRI.

Experimental Example 2

Confirmation of Biological Activity of Met-TNFRI and Met-TNFRI Mutants by WEHI Cytotoxicity Assay The purified Met-TNFRI and Met-TNFRI mutants were quantified using a Bradford method and were applied to WEHI cells (ATCC, Cat. No: CRL-2148), which are sensitive to a predetermined concentration of TNF-α, to measure the protection of the cells from a cytotoxic effect, thereby confirming that the Met-TNFRI and Met-TNFRI mutants has biological activity.

The WEHI cell has a cell having sensitivity and may be protected from the cytotoxic effect in a presence of TNF-α

TABLE 3

Measurement of affinity of mutant using ELISA method

| Variants No. | Result Affinity (%) | Variants No. | Result Affinity (%) |
|---|---|---|---|
| Wild-type (TNFRI126) | 100 | Wild-type (TNFRI126) | 100 |
| TNFRI126-1 | 324 | TNFRI126-16 | 882 |
| TNFRI126-2 | 829 | TNFRI126-17 | 771 |
| TNFRI126-3 | 341 | TNFRI126-18 | 1012 |
| TNFRI126-4 | 524 | TNFRI126-19 | 482 |
| TNFRI126-5 | 712 | TNFRI126-20 | 782 |
| TNFRI126-6 | 741 | TNFRI126-21 | 1404 |
| TNFRI126-7 | 600 | TNFRI126-22 | 1434 |
| TNFRI126-8 | 865 | TNFRI126-23 | 1105 |
| TNFRI126-9 | 941 | TNFRI126-24 | 1059 |
| TNFRI126-10 | 800 | TNFRI126-25 | 682 |
| TNFRI126-11 | N/A | TNFRI126-26 | 1141 |
| TNFRI126-12 | 659 | TNFRI126-27 | 894 |
| TNFRI126-13 | 806 | TNFRI126-28 | N/A |
| TNFRI126-14 | 765 | TNFRI126-29 | 435 |
| TNFRI126-15 | 941 | TNFRI126-30 | 952 | inhibitor to thereby be proliferated. It was confirmed that the Met-TNFRI and Met-TNFRI mutants has biological activity by the WEHI Cytotoxicity assay.

Figure 4:
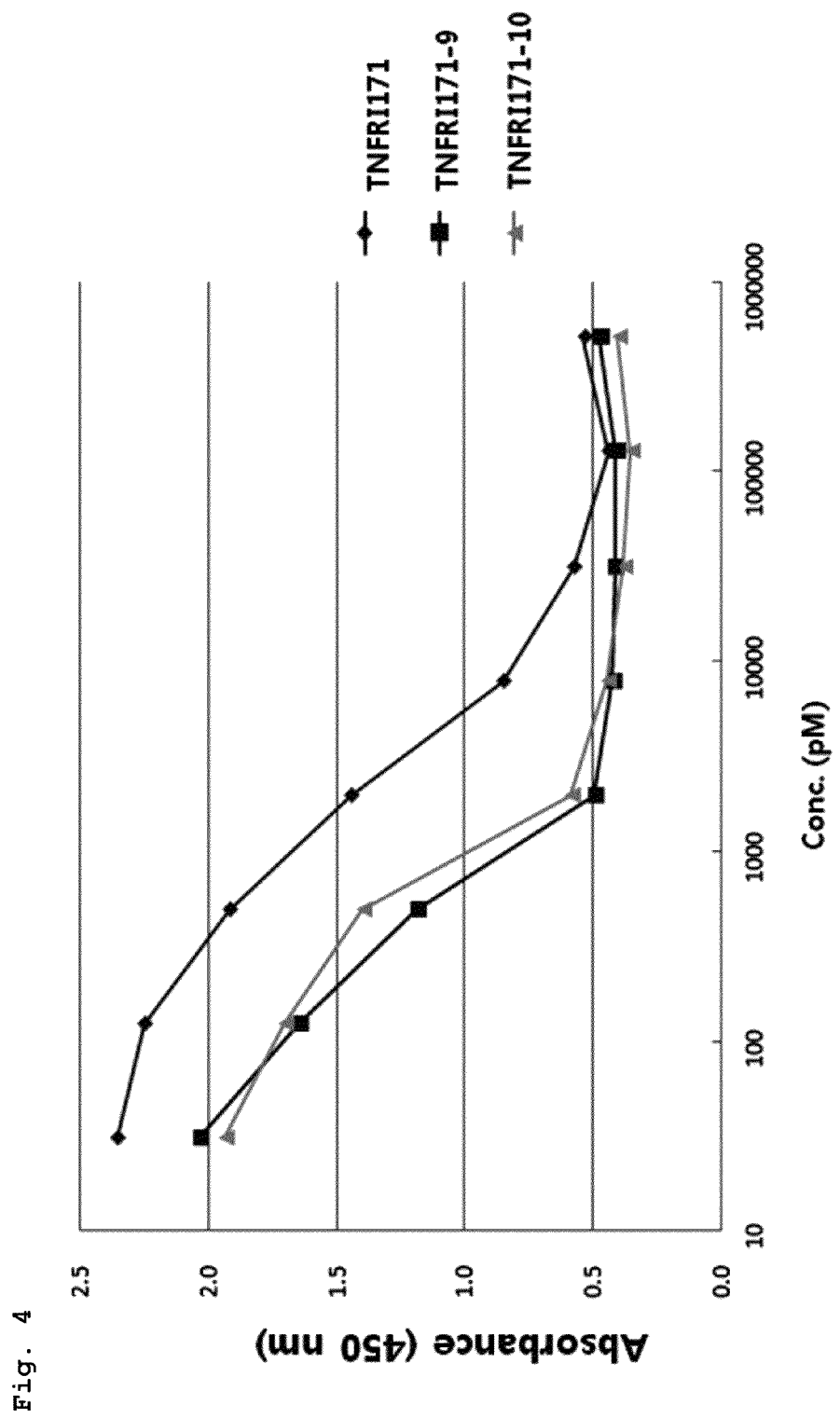
Figure 5:
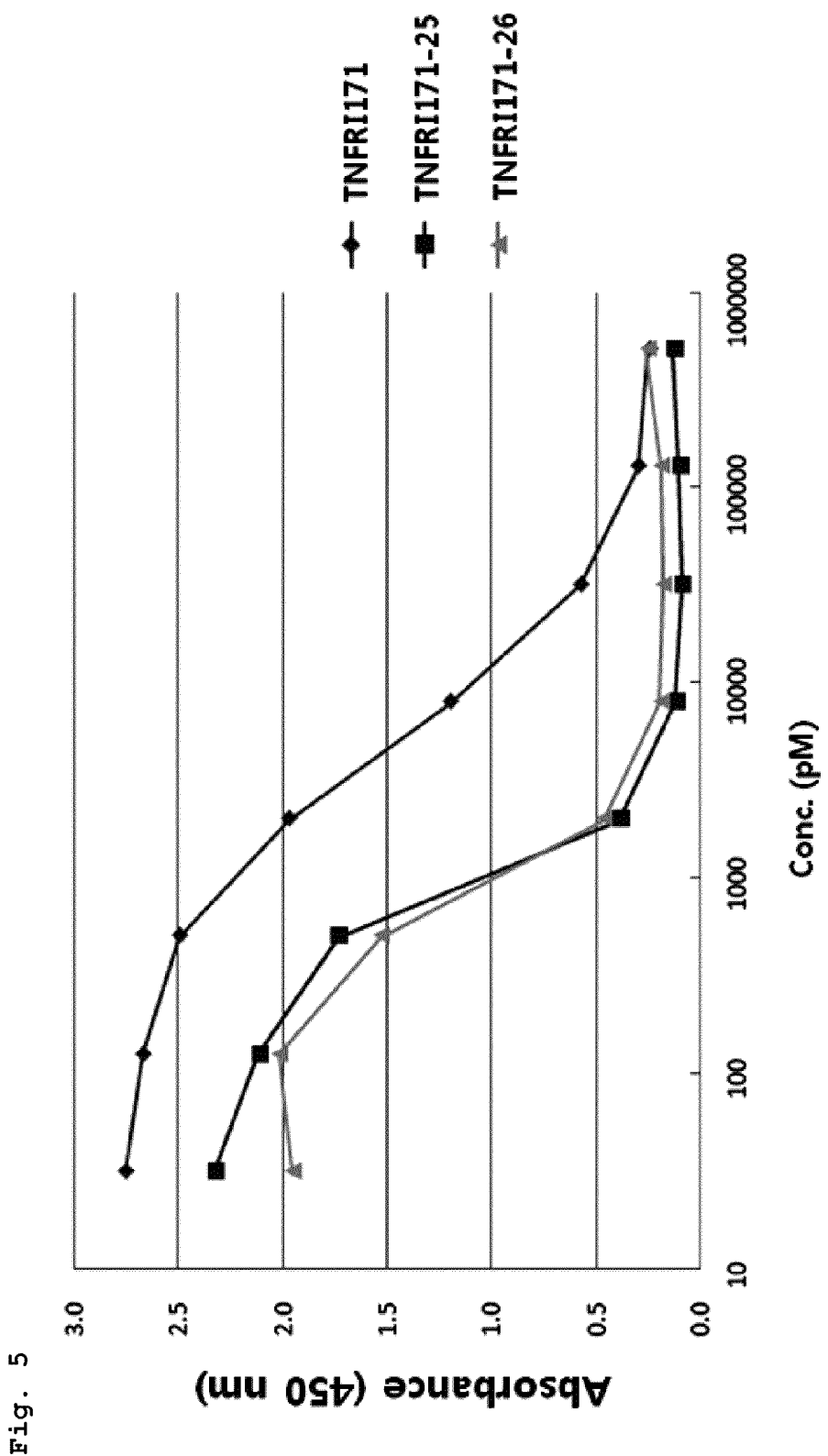

Specifically, WEHI (ATCC, Cat. No: CRL-2148) cells were suspended at a density of $2 \times 10^5$ cells/ml in RPMI medium supplemented with 5% fetal bovine serum, penicillin (50 U/ml), and streptomycin (50 mg/ml). The cell suspension was plated in the amount of 100 μL/well into 96-well microtiter plates and cultured at 37° C. for 24 hours in 5% CO2 atmosphere. 100 μL of 70 pg/mL TNF-α using a medium containing actinomycin-D was added to each well. Then, 100 μg/mL of each mutant sample was diluted from 3.0 nM to 0.18 pM using PBS solution, and added to each well containing TNF-α. In this case, Enbrel (Amgen, chemical name: etanercept) was applied at a concentration from 0.04 pM to 3.0 nM while the wild-type TNFRI was used at a concentration from 12 pM to 200 nM. The WEHI cells were cultured at 37° C. for 24 hours in 5% CO2 atmosphere. Next, an MTT reagent present in MTT assay kit for analyzing cell proliferation (Roche, Cat. No: 11455007001) was added to each well and further cultured for 4 to 6 hours. A solubilizing reagent was added to each well. After culturing the cell for 24 hours, dissolution of the purple formazan was identified, and then absorbance at 570 nm was read on a Vmax reader. Activities of the Met-TNFRI and the Met-TNFRI mutants were determined by measuring ND50 values through absorbance change with concentrations and calculating relative activity to the wild-type TNFRI. The result was shown in the following Table 4. Data of the representative mutants (TNFRI126-30, TNFRI171-2, TNFRI171-8, TNFRI171-9, TNFRI171-10, TNFRI171-15, TNFRI171-16, TNFRI171-18, TNFRI171-21, TNFRI171-22, and TNFRI171-30) were shown in FIGS. 4 to 6.

Figure 6:
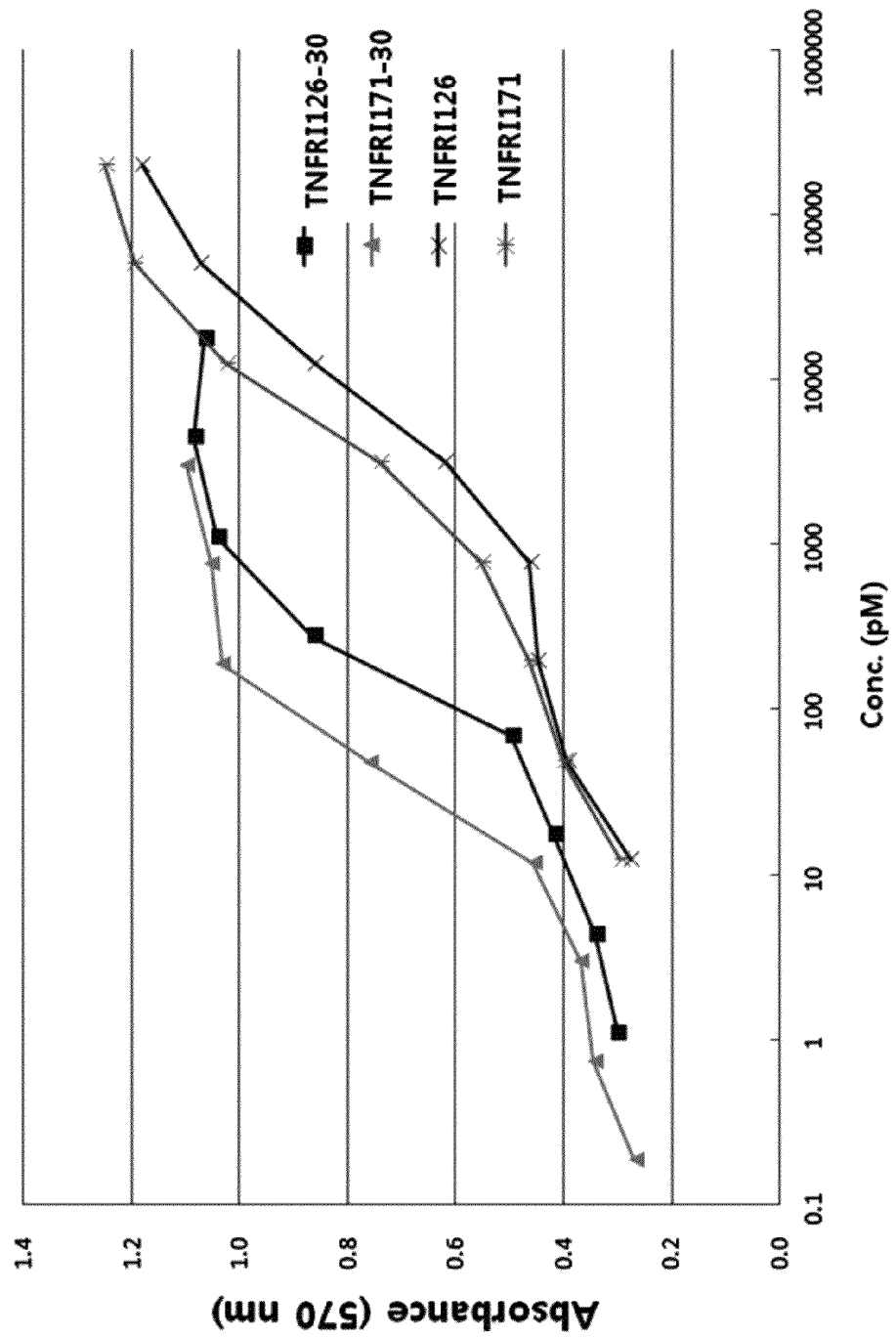
Figure 7:
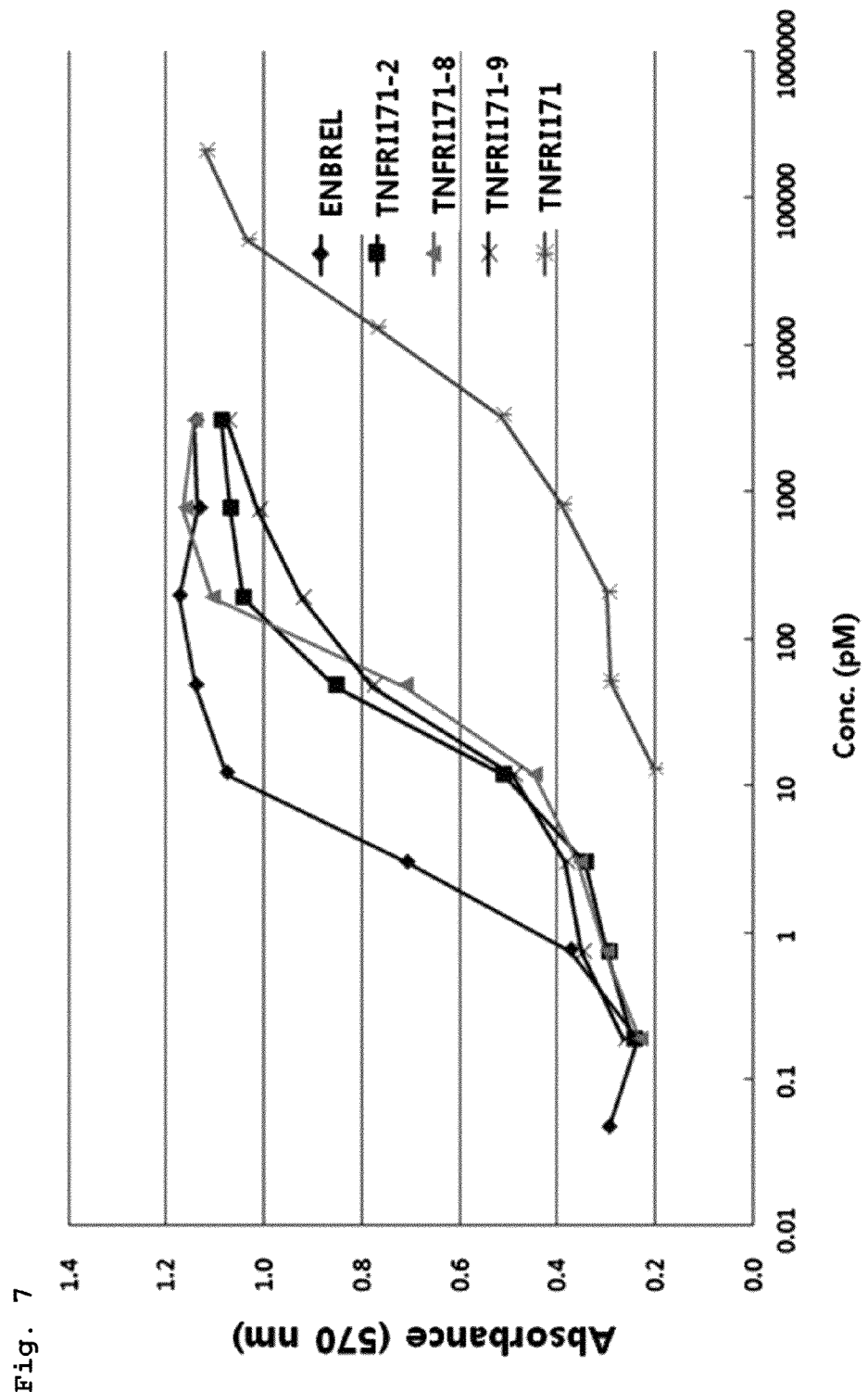
Figure 8:
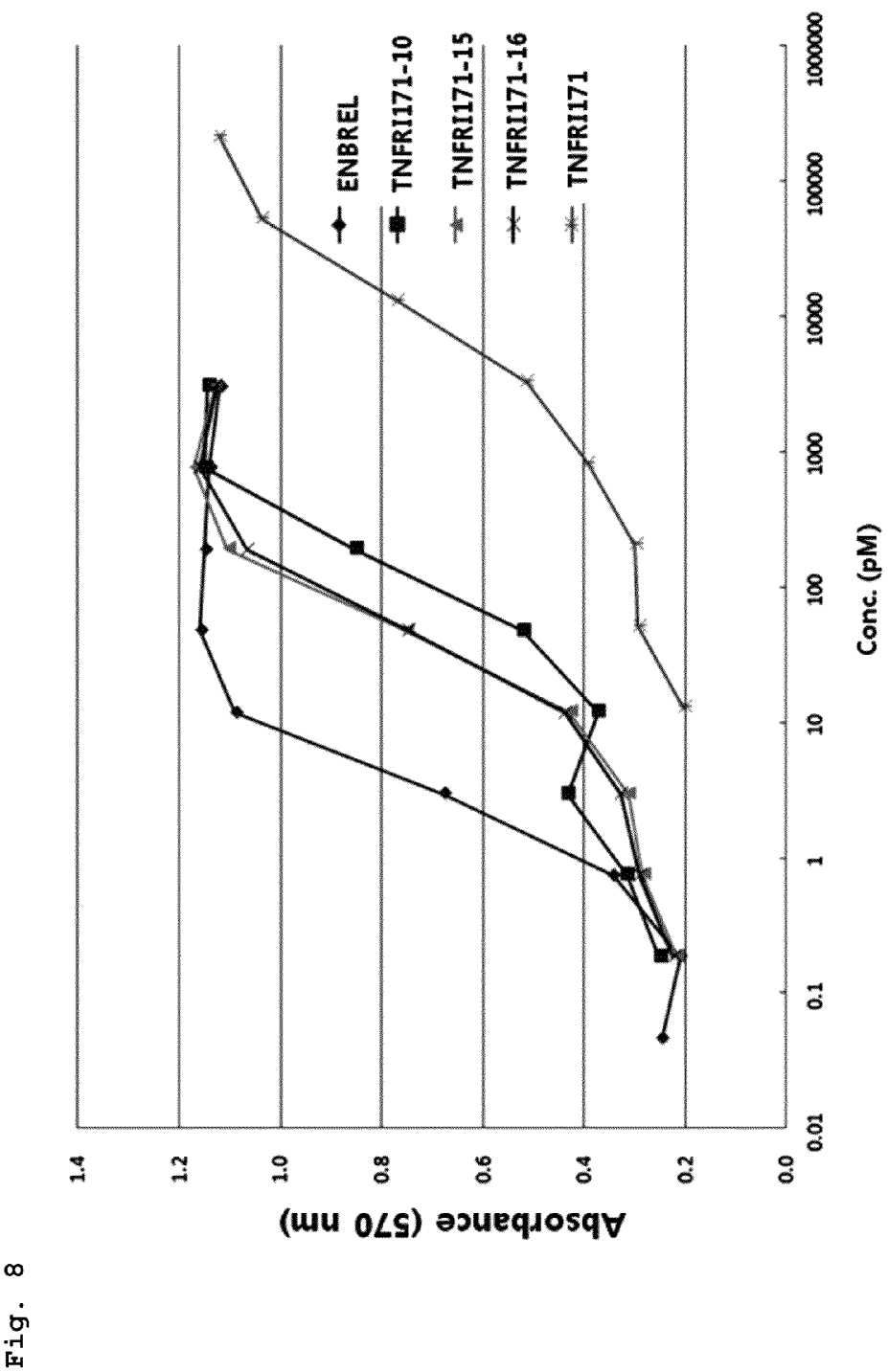
Figure 9:
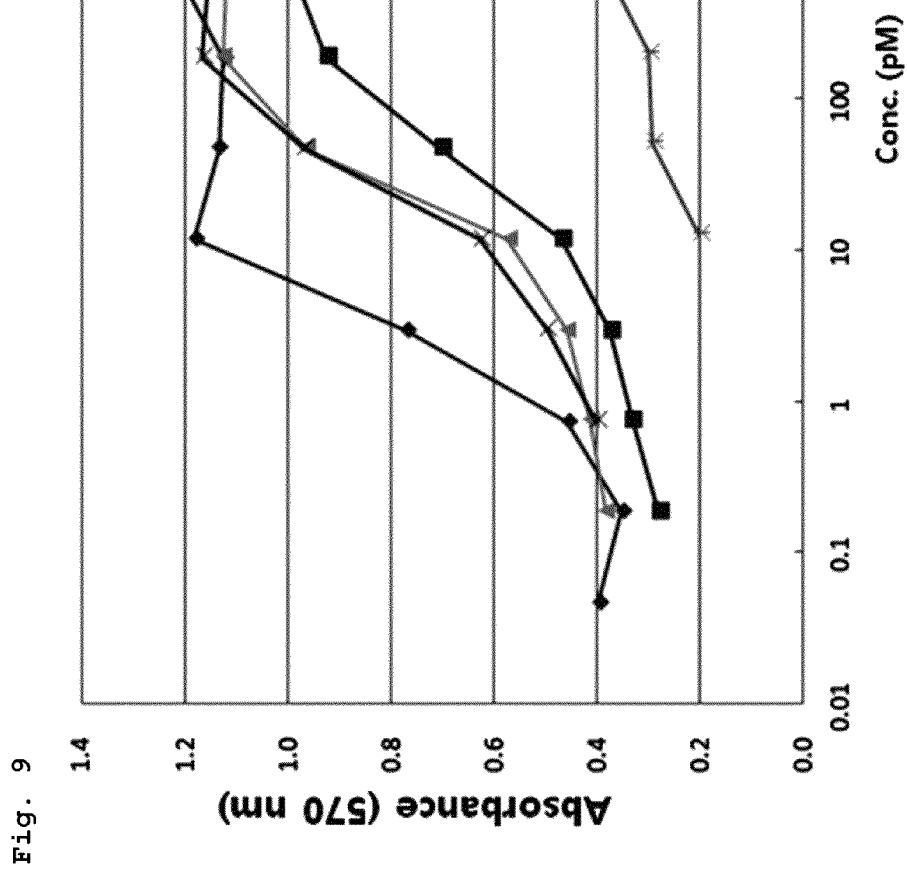

Particularly, as shown in FIG. 6, TNFRI126 and TNFRI171 were observed to exhibit substantially the same effect. Further, as a result of the WEHI cytotoxicity assay, in the case of Met-TNFRI and the Met-TNFRI mutants, the biological activity of TNFRI171-2, TNFRI171-21, and TNFRI171-22 were 200-fold higher than that of the wild-type TNFRI that of the wild-type TNFRI. (Table 4)

TABLE 4

Measurement of biological activity of mutant by cytotoxicity assay

| Variants No. | Relative activity (cell based assay) (Folds) |
|---|---|
| Wild-type (TNFRI171) | 1 |
| TNFRI171-1 | 127 |
| TNFRI171-2 | 207 |
| TNFRI171-8 | 120 |
| TNFRI171-9 | 158 |
| TNFRI171-10 | 44 |
| TNFRI171-15 | 142 |
| TNFRI171-16 | 139 |
| TNFRI171-18 | 126 |
| TNFRI171-26 | 196 |
| TNFRI171-21 | 226 |
| TNFRI171-22 | 242 |

---

What is claimed is:

1. A modified human tumor necrosis factor receptor-I (TNFRI) polypeptide or fragment thereof comprising an amino acid sequence selected from the group consisting of:
   i) the amino acid sequence of natural TNFRI as set forth in SEQ ID NO: 1;
   ii) the amino acid sequence composed of amino acid residues 41 to 211 of the amino acid sequence of the natural TNFRI set forth in SEQ ID NO: 1 (TNFRI171);
   iii) the amino acid sequence composed of amino acid residues 41 to 166 of the amino acid sequence of the natural TNFRI set forth in SEQ ID NO: 1 (TNFRI126); and
   iv) the amino acid sequence composed of amino acid residues 41 to 145 of the amino acid sequence of the natural TNFRI set forth in SEQ ID NO: 1 (TNFRI105);
   wherein the amino acid sequence is modified at least at positions 92, 95, 97 and 98.

2. The modified human tumor necrosis factor receptor-I polypeptide or a fragment thereof according to claim 1,
   wherein the modified human tumor necrosis factor receptor-I polypeptide or a fragment further comprises amino acid modification at position 93.

3. The modified human tumor necrosis factor receptor-I polypeptide or a fragment thereof according to claim 1,
   wherein the amino acid modification at each of positions 92, 95, 97 and 98 is;
   i) substitution of S with I, L, F, M, W, Q, T, Y, K, H, E, A, V, P, N or R at position 92;
   ii) substitution of H with F at position 95;
   iii) substitution of R with P, L or I at position 97; and
   iv) substitution of H with A or G at position 98.

4. The modified human tumor necrosis factor receptor-I polypeptide or a fragment thereof according to claim 3,
   wherein the modified human tumor necrosis factor receptor-I polypeptide or a fragment further comprises amino acid modification of substitution of E with P at position 93.

5. The modified human tumor necrosis factor receptor-I polypeptide or a fragment thereof according to claim 3,
   wherein the amino acid substitution is selected from S92I/H95F/R97P/H98A, S92F/H95F/R97P/H98A, S92M/H95F/R97P/H98A, S92W/H95F/R97P/H98A, S92Y/H95F/R97P/H98A, S92K/H95F/R97P/H98A, S92H/H95F/R97P/H98A, S92I/H95F/R97P/H98G, and S92M/H95F/R97P/H98G.

6. The modified human tumor necrosis factor receptor-I polypeptide or a fragment thereof according to claim 3,
   wherein the amino acid substitution is selected from S92I/H95F/R97P/H98A, S92M/H95F/R97P/H98A, S92I/H95F/R97P/H98G, and S92M/H95F/R97P/H98G.

7. The modified human tumor necrosis factor receptor-I polypeptide or a fragment thereof according to claim 3,
   comprising an amino acid sequence selected from SEQ ID NOs: 10, 12-18, 20-26, 28-35, 37, 38, 40, 41-48, 50-56, 58-65, 67, 68, 70, 72-78, 80-86, 88-95, 97, and 98.

8. A modified TNFRI polypeptide having sequence homology of more than 90%, more than 95%, more than 96%, more than 97%, more than 98% or more than 99% to the amino acid sequence as set forth in SEQ ID NO: 1, the modified TNFRI polypeptide or a fragment thereof comprising modifications corresponding to positions 92, 95, 97 and 98 in the amino acid sequence,
   wherein the amino acid modification at each position is:
   i) substitution of S with I, F, M, W, Y, K or H position 92;
   ii) substitution of H with F at position 95;
   iii) substitution of R with P, L or I at position 97; and
   iv) substitution of H with A or G at position 98.

9. A polypeptide complex comprising at least two modified TNFRI polypeptides or fragments thereof according to claim 1 linked by a covalent bond.

10. The modified human tumor necrosis factor receptor-I polypeptide or a fragment thereof according to claim 1, wherein the modified TNFRI polypeptide or fragment thereof contains an additional modification of glycosylation, acylation, methylation, phosphorylation, hesylation, carbamylation, sulfation, prenylation, oxidation, guanidination, amidination, carbamylation, trinitrophenylation, nitration or PEGylation.

11. A gene comprising a nucleotide sequence encoding the modified TNFRI polypeptide or fragment thereof of claim 1.

12. The gene according to claim 11, wherein the gene has the sequence of SEQ ID NO: 5 in which a codon is optimized to be suitable for expression in *E. coli*.

13. A vector comprising the gene of claim 11.

14. A cell transformed with the vector of claim 13.

15. The cell according to claim 14, wherein the cell is *E. coli*.

16. A pharmaceutical preparation comprising the modified TNFRI polypeptide or fragment thereof of claim 1.

17. A method for producing a modified TNFRI polypeptide or fragment thereof, comprising using the gene of claim 11 or a vector containing the same gene.

18. The modified human tumor necrosis factor receptor-I polypeptide or a fragment thereof according to claim 7, wherein the amino acid sequence is SEQ ID NO: 90.

* * * * *